(12) United States Patent
Rubnov et al.

(10) Patent No.: US 9,994,522 B2
(45) Date of Patent: Jun. 12, 2018

(54) AMORPHOUS FORM OF APREMILAST

(71) Applicant: MAPI PHARMA LTD., Ness Ziona (IL)

(72) Inventors: Shai Rubnov, Tel Aviv (IL); Ehud Marom, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days. days.

(21) Appl. No.: 15/308,740

(22) PCT Filed: Jul. 20, 2014

(86) PCT No.: PCT/IL2014/050658
§ 371 (c)(1),
(2) Date: Nov. 3, 2016

(87) PCT Pub. No.: WO2015/173792
PCT Pub. Date: Nov. 19, 2015

(65) Prior Publication Data
US 2017/0174626 A1   Jun. 22, 2017

Related U.S. Application Data

(60) Provisional application No. 61/991,528, filed on May 11, 2014.

(51) Int. Cl.
*C07D 209/48* (2006.01)
(52) U.S. Cl.
CPC .................................. *C07D 209/48* (2013.01)
(58) Field of Classification Search
CPC .................................................... C07D 209/48
See application file for complete search history.

(56) References Cited

U.S. PATENT DOCUMENTS

| | | | |
|---|---|---|---|
| 5,635,517 | A | 6/1997 | Muller |
| 5,654,312 | A | 8/1997 | Andrulis, Jr. |
| 6,011,050 | A | 1/2000 | Muller et al. |
| 6,020,358 | A | 2/2000 | Muller et al. |
| 6,281,230 | B1 | 8/2001 | Muller |
| 6,962,940 | B2 | 11/2005 | Muller et al. |
| 7,427,638 | B2 | 9/2008 | Muller et al. |
| 7,893,101 | B2 | 2/2011 | Muller et al. |
| 8,629,173 | B2 | 1/2014 | Muller et al. |

FOREIGN PATENT DOCUMENTS

| | | |
|---|---|---|
| AU | 2003224729 B2 | 1/2008 |
| EP | 1126839 B1 | 1/2007 |
| EP | 1 752 148 A2 | 2/2007 |
| EP | 2 074 995 A1 | 7/2009 |
| EP | 1485087 B1 | 8/2009 |
| EP | 2 223 687 A1 | 9/2010 |
| EP | 2 223 688 A1 | 9/2010 |
| EP | 2 295 055 A2 | 3/2011 |
| EP | 2 311 453 A1 | 4/2011 |
| EP | 2 420 490 A1 | 2/2012 |
| EP | 2305248 B1 | 5/2013 |
| EP | 2 962 690 A1 | 1/2016 |
| IL | 164147 B | 11/2010 |
| IL | 239499 | 8/2015 |
| IL | 222844 | 8/2016 |
| IL | 234135 | 6/2017 |
| IL | 252459 | 7/2017 |
| IL | 229079 | 12/2017 |
| WO | 87/00066 A1 | 1/1987 |
| WO | 00/25777 A1 | 5/2000 |
| WO | 03/080048 A1 | 10/2003 |
| WO | 03/080049 A1 | 10/2003 |
| WO | 2004/060313 A2 | 7/2004 |
| WO | 2005110085 A2 | 11/2005 |
| WO | 2009/120167 A1 | 10/2009 |
| WO | 2012/083017 A2 | 6/2012 |
| WO | 2013/101810 A1 | 7/2013 |
| WO | 2014/072259 A1 | 5/2014 |

OTHER PUBLICATIONS

Meningitis [online], retrieved from the internet on Sep. 29, 2017. URL; <http://www.mayoclinic.org/diseases-conditions/meningitis/home/ovc-20169520?p1>.*
Akazome et al., (1997) Asymmetric recognition of 1-arylethylamines by (R)-phenylglycyl-(R)-phenylglycine and its mechanism. Tetrahedron: Asymmetry, 8(14), 2331-2336.
Ariëns, (1986) Stereochemistry: a source of problems in medicinal chemistry. Medicinal research reviews, 6(4), 451-466.
Bartlett et al., (2004) The evolution of thalidomide and its IMiD derivatives as anticancer agents. Nature Reviews Cancer, 4(4), 314-322.
Bentley et al., (2006) The nose as a stereochemist. Enantiomers and odor. Chemical reviews, 106(9), 4099-4112.
Celgene Corporation press release, Positive phase topline clinical data for Celgene oral compound Apremilast (CC-10004) reported for patients with moderate to severe Psoriasis, Dec. 15, 2009; 3 pages.
Eriksson et al., (2001) Clinical pharmacology of thalidomide. European journal of clinical pharmacology, 57(5), 365-376.
Evans et al., (1988) Stereoselective drug disposition: potential for misinterpretation of drug disposition data. British journal of clinical pharmacology, 26(6), 771-780.
Gottlieb et al (2008) an open-label, single-arm pilot study in patients with severe plaque-type psoriasis treated with an oral anti-inflammatory agent, apremilast. Current medical research and opinion, 24(5), 1529-1538.

(Continued)

*Primary Examiner* — Shawquia Jackson
(74) *Attorney, Agent, or Firm* — Rothwell, Figg, Ernst & Manbeck, P.C.

(57) ABSTRACT

The present invention provides a new amorphous form of apremilast, pharmaceutical compositions comprising same, methods for preparation and use thereof in treating conditions mediated by inhibition of TNF-α production or inhibition of phosphodiesterase 4 (PDE4), e.g., psoriatic arthritis and other chronic inflammatory diseases.

20 Claims, 22 Drawing Sheets

(56) References Cited

OTHER PUBLICATIONS

Hancock et al., (2002) Polyamorphism: a pharmaceutical science perspective. Journal of pharmacy and pharmacology, 54(8), 1151-1152.
Jamali et al., (1989) Enantioselective aspects of drug action and disposition: therapeutic pitfalls. Journal of Pharmaceutical Sciences, 78(9), 695-715.
Luke & Holt, (1999) Synthesis of (S)-5-(1-aminoethyl)-2-(cyclohexylmethoxy) benzamide. Tetrahedron: Asymmetry, 10(22), 4393-4403.
Marriott et al., (1998) CC-3052: a water-soluble analog of thalidomide and potent inhibitor of activation-induced TNF-α production. The Journal of Immunology, 161(8), 4236-4243.
McCann et al., (2010) Apremilast, a novel PDE4 inhibitor, inhibits spontaneous production of tumour necrosis factor-alpha from human rheumatoid synovial cells and ameliorates experimental arthritis. Arthritis research & therapy, 12(3), 1-11.
Schafer et al., (2010) Apremilast, a cAMP phosphodiesterase-4 inhibitor, demonstrates anti-inflammatory activity in vitro and in a model of psoriasis. British journal of pharmacology, 159(4), 842-855.
Schafer et al., (2014) Apremilast is a selective PDE4 inhibitor with regulatory effects on innate immunity. Cellular signalling, 26(9), 2016-2029.
Simonyi, (1984) on chiral drug action. Medicinal research reviews, 4(3), 359-413.
Triggle, (1997) Stereoselectivity of drug action. Drug Discovery Today, 2(4), 138-147.
Andersson et al., (2001) Pharmacokinetics and pharmacodynamics of esomeprazole, the S-isomer of omeprazole. Aliment Pharmacology & Therapeutics, 15(10), 1563-1569.
Ariens, (1984) Stereochemistry, a basis for sophisticated nonsense in pharmacokinetics and clinical pharmacology. European Journal of Clinical Pharmacology, 26(6), 663-668.
Devalia et al., (2001) A randomized, double-blind, crossover comparison among cetirizine, levocetirizine, and ucb 28557 on histamine-induced cutaneous responses in healthy adult volunteers. Allergy, 56(1), 50-57.
Ettehadi et al., (1994) Elevated tumour necrosis factor-alpha (TNF-α) biological activity in psoriatic skin lesions. Clinical & Experimental Immunology, 96(1), 146-151.
FDA Guidelines for Submitting Supporting Documentation in Drug Applications for the Manufacture of Drug Substances, Feb. 1987, 48 pages.
Fearon & Veale, (2001) Pathogenesis of psoriatic arthritis. Clinical and Experimental Dermatology, 26(4), 333-337.
Food and Drug Administration, (1992) FDA's policy statement for the development of new stereoisomeric drugs. 57 Fed. Reg. 22, 249.
Latner, (2001) Top 200 drugs by retail sales in 2000. Drug Topics, 6(18), 1985-1999.
Lebwohl & Ali, (2001) Treatment of psoriasis. Part 1. Topical therapy and phototherapy. Journal of the American Academy of Dermatology, 45(4), 487-502.
Lipinski et al., (1996) Experimental and computational approaches to estimate solubility and permeability in drug discovery and development settings. Advanced Drug Delivery Reviews, 23(1-3), 3-26.
Martin & Bustamante (1993) in: Physical pharmacy : physical chemical principles in the pharmaceutical sciences; p. 512-530. Philadelphia Lea & Febiger.
McGoven (2014) Center for Drug Evaluation and Research,Application No. 205437Orig1s000, Pharmacology Review(s). p. 41.
Mease, (2001) Cytokine blockers in psoriatic arthritis. Annals of the Rheumatic Diseases, 60(suppl 3), iii37-iii40.
Nelson et al., (1998) Improved bronchodilation with levalbuterol compared with racemic albuterol in patients with asthma. Journal of Allergy and Clinical Immunology, 102(6), 943-952.
Nunez et al., (2009) Homochiral drugs: a demanding tendency of the pharmaceutical industry. Current Medicinal Chemistry, 16(16), 2064-2074.
Peters et al., (2000) Pathophysiology and treatment of psoriasis. American Journal of Health System Pharmacy, 57(7), 645-662.
Guillory, (1999) Generation of polymorphs, hydrates, solvates, and amorphous solids. Drugs and the pharmaceutical sciences, 95, 183-225.

* cited by examiner

AMORPHOUS FORM OF APREMILAST

CROSS-REFERENCE TO RELATED APPLICATIONS

The present application is a national stage filing under 35 U.S.C. § 371 of PCT/IL2014/050658, filed on Jul. 20, 2014, and claims the benefit of priority to U.S. Provisional Application No. 61/991,528, filed on May 11, 2014. Each application is incorporated herein by reference in its entirety.

FIELD OF THE INVENTION

The present invention provides a new amorphous form of apremilast, pharmaceutical compositions comprising same, methods for preparation and use thereof in treating conditions mediated by inhibition of TNF-α production or inhibition of phosphodiesterase 4 (PDE4), e.g., psoriatic arthritis and other chronic inflammatory diseases.

BACKGROUND OF THE INVENTION

Apremilast is a selective inhibitor of phosphodiesterase 4 (PDE4) specific for cyclic adenosine monophosphate (cAMP). The inhibition of PDE4 results in increased intracellular cAMP levels. Apremilast is chemically named N-[2-[(1S)-1-(3-ethoxy-4-methoxyphenyl)-2-(methylsulfonyl)ethyl]-2,3-dihydro-1,3-dioxo-1H-isoindol-4-yl]acetamide, and is represented by the following chemical structure:

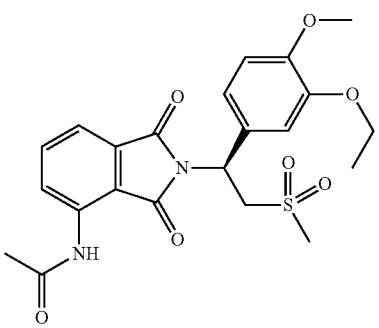 [SMILES: CCOc1cc([C@@H](CS(C)(=O)=O)N2C(=O)c3cccc(NC(C)=O)c3C2=O)ccc1OC]

Apremilast is approved in the United States for treatment of adults with active psoriatic arthritis. It is also being tested for treating other chronic inflammatory diseases such as psoriasis, ankylosing spondylitis, Behcet's disease, and rheumatoid arthritis. The specific mechanism(s) responsible to the apremilast's therapeutic action in psoriatic arthritis patients is not well defined.

U.S. Pat. No. 6,020,358 discloses substituted phenethylsulfones, including apremilast, and methods of use thereof for reducing TNFα levels.

WO 2003/080048 and WO 2003/080049 disclose the use of the (−) and (+) enantiomers of apremilast, respectively, in the treatment or prevention of diseases or disorders by the inhibiting TNF-α production or PDE4.

WO 2009/120167 discloses seven solid forms of the (+) enantiomer of apremilast, designated as Forms A to G, including methods of preparation. The crystalline form A is characterized by diffraction peaks in the X-ray powder diffraction pattern at 8.1°, 15.2°, 17.4°, 23.6° and 25.1° degrees 2θ. The crystalline form B is characterized by diffraction peaks in the X-ray powder diffraction pattern at 10.1°, 13.5°, 20.7° and 26.9° degrees 2θ. The crystalline form C is characterized by peaks in the X-ray powder diffraction pattern at 7.5°, 11.3°, 16.4°, 17.8° and 26.4° degrees 2θ. The crystalline form D is characterized by diffraction peaks in the X-ray powder diffraction pattern at 7.5°, 11.3°, 16.3°, 25.2° and 26.0° degrees 2θ. The crystalline form E is characterized by peaks in the X-ray powder diffraction pattern at 7.6°, 9.2°, 11.4°, 17.9° and 26.6° degrees 2θ. The crystalline form F is characterized by diffraction peaks in the X-ray powder diffraction pattern at 8.1°, 8.6°, 15.6°, 17.3° and 25.4° degrees 2θ. The crystalline form G is characterized by diffraction peaks in the X-ray powder diffraction pattern at 7.9°, 11.7°, 16.8°, 18.1° and 26.7° degrees 2θ. WO 2009/120167 also generally mentions an amorphous form of apremilast but does not teach that a single amorphous form was actually obtained or characterized.

A new crystalline or amorphous form of a compound may possess physical properties that differs from, and is advantageous over, those of other crystalline or amorphous forms. These include, packing properties such as molar volume, density and hygroscopicity; thermodynamic properties such as melting temperature, vapor pressure and solubility; kinetic properties such as dissolution rate and stability under various storage conditions; surface properties such as surface area, wettability, interfacial tension and shape; mechanical properties such as hardness, tensile strength, compatibility, handling, flow and blend; and filtration properties. Variations in any one of these properties may affect the chemical and pharmaceutical processing of a compound as well as its bioavailability and may often render the new form advantageous for pharmaceutical and medical use.

There remains an unmet need for additional solid state forms of apremilast having good physiochemical properties, desirable bioavailability, and advantageous pharmaceutical parameters.

SUMMARY OF THE INVENTION

The present invention provides a new amorphous form of apremilast, pharmaceutical compositions comprising same, methods for its preparation and use thereof in treating conditions mediated by reduction in the levels of TNF-α or inhibition of PDE4, in particular, psoriatic arthritis and other chronic inflammatory diseases.

The present invention is based in part on the unexpected finding that the new amorphous form disclosed herein possesses advantageous physical and/or chemical properties which render its manufacturing, processing, formulation and storage as medicament beneficial. This form has a good bioavailability as well as desirable stability characteristics which enable its incorporation into a variety of different formulations that are particularly suitable for pharmaceutical utility. The present invention also provides processes for preparing amorphous apremilast, as described herein. The invention further provides an amorphous apremilast prepared by such processes.

According to one aspect, the present invention provides a process for preparing an amorphous apremilast, comprising the steps of:

(a) heating apremilast to melt under vacuum; and (b) cooling the melted apremilast obtained in step (a), so as to provide amorphous apremilast.

According to some embodiments, the cooling in step (b) is selected from fast cooling and slow cooling. Each possibility represents a separate embodiment of the invention.

The invention further provides an amorphous apremilast prepared by the above-described process.

According to another aspect, the present invention provides a process for preparing an amorphous apremilast, the process comprising the steps of:
(a) dissolving apremilast in a solvent or a mixture of solvents selected from THF, acetone and DMF:EtOH; and
(b) slowly evaporating the solvent or a mixture of solvents so as to precipitate amorphous apremilast.

According to some embodiments, the DMF:EtOH is used at a volume ratio of about 1:3.

The invention further provides an amorphous apremilast prepared by the above-described process.

According to yet another aspect, the present invention provides a process for preparing an amorphous apremilast, the process comprising the steps of:
(a) dissolving apremilast in a solvent selected from acetone, THF and MEK to obtain an apremilast solution; and
(b) combining the apremilast solution with an anti-solvent selected from water and heptane so as to precipitate amorphous apremilast.

In one embodiment, the apremilast solution is added to the anti-solvent. In another embodiment, the anti-solvent is added to the apremilast solution. In another embodiment, the volume ratio of solvent to anti-solvent is about 1 to about 10. In one currently preferred embodiment, the solvent/anti-solvent mixture is heptane and acetone, wherein heptane is added to acetone. In another currently preferred embodiment, the solvent/anti-solvent mixture is heptane and acetone, wherein acetone is added to heptane. In another currently preferred embodiment, the solvent/anti-solvent mixture is heptane and MEK, preferably wherein the heptane is added to MEK. In another currently preferred embodiment, the solvent/anti-solvent mixture is THF and heptane, preferably wherein the THF is added to heptane. In another currently preferred embodiment, the solvent/anti-solvent mixture is water and acetone, preferably wherein the water is added to acetone. In another currently preferred embodiment, the process for preparing an amorphous apremilast further comprises the step of drying the apremilast obtained in step (b) under vacuum at a temperature of about 25° C.

The invention further provides an amorphous apremilast prepared by the above-described process.

According to an additional aspect, the present invention provides a process for preparing an amorphous apremilast, the process comprising the steps of:
(a) heating apremilast to a temperature of about 120° C.; and
(b) cooling the apremilast obtained in step (a) to about 25° C., so as to provide amorphous apremilast.

The invention further provides an amorphous apremilast prepared by the above-described process.

According to another aspect, the present invention provides an amorphous form of apremilast. In one embodiment, the amorphous apremilast is characterized by an X-ray diffraction (XRD) profile substantially as shown in any of the FIG. 1, 4, 7, 10, 13, 20, 23, 27, 28, 29 or 30. Each possibility represents a separate embodiment of the present invention. In another embodiment, the present invention provides amorphous form of apremilast characterized by a modulated DSC (mDSC) profile substantially as shown in any of the FIG. 2, 5, 8, 11A, 11B, 14, 16, 18, 21, 24, 31, 32, 33, 34 or 35, or a DSC profile substantially as shown in FIG. 36. Each possibility represents a separate embodiment of the present invention. In another embodiment, the amorphous apremilast has a glass transition temperature between about 36° C. and about 79° C., for example about 36.1° C., 38.0° C., 41.9° C., 44.1° C., 48.2° C., 60.9° C., 75.9° C., 77.2° C., 77.7° C., 78.2° C., or about 133.6° C. Each possibility represents a separate embodiment of the present invention. In yet another embodiment, the amorphous apremilast is characterized by a TGA profile substantially as shown in any of the FIG. 3, 6, 9, 12, 15, 17, 19, 22 or 25. Each possibility represents a separate embodiment of the present invention. In another embodiment, the amorphous apremilast of the present invention is further characterized by a Dynamic Vapor Sorption (DVS) profile substantially as shown in FIGS. 26A and 26B. Each possibility represents a separate embodiment of the present invention.

According to another aspect, the present invention provides a pharmaceutical composition comprising as an active ingredient the amorphous apremilast as described herein, and a pharmaceutically acceptable carrier.

In one currently preferred embodiment, the pharmaceutical composition is in the form of a tablet. According to some embodiments, the amorphous apremilast of the present invention is useful for treating a medical condition mediated TNFα or by PDE4.

According to a further aspect, the present invention provides a method of treating a medical condition mediated by TNFα or by PDE4 comprising administering to a subject in need thereof an effective amount of the amorphous apremilast of the present invention, or a pharmaceutical composition comprising said amorphous apremilast.

In additional embodiments, the present invention provides the use of the amorphous apremilast of the present invention for treating medical conditions mediated by TNFα or PDE4.

According to some embodiments, the medical condition is selected from the group consisting of psoriasis, psoriatic arthritis, ankylosing spondylitis, Behcet's disease, and rheumatoid arthritis.

According to some embodiments, the subject in need is mammal, preferably a human.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 11 illustrates a characteristic modulated Differential Scanning calorimetry (mDSC) profile of an amorphous form of apremilast obtained by method II.

FIG. 26 illustrates a characteristic Dynamic Vapor Sorption (DVS) isotherm plot of an amorphous form of apremilast obtained by scaled-up method III (addition of water to acetone).

DETAILED DESCRIPTION OF THE INVENTION

Figure 1:
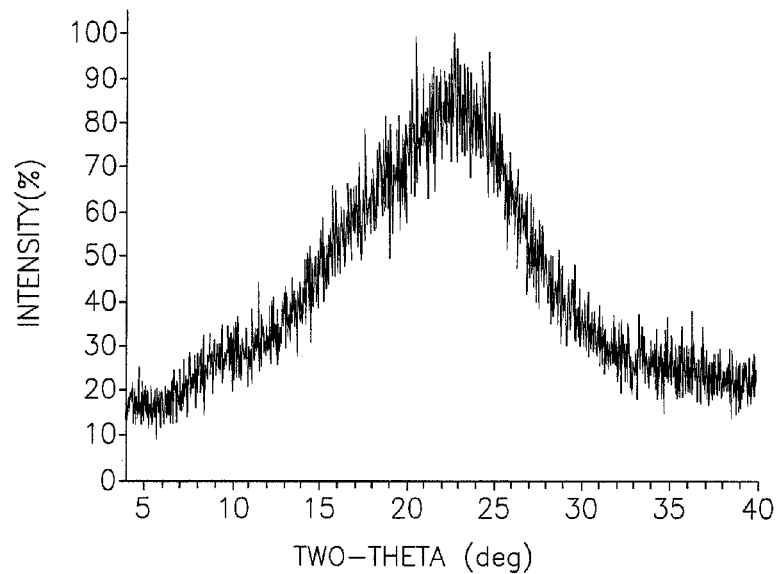
FIG. 1 illustrates a characteristic X-ray diffraction pattern of an amorphous form of apremilast obtained by method I (in THF).

The present invention is directed to a novel amorphous form of N-[2-[(1S)-1-(3-ethoxy-4-methoxyphenyl)-2-(methylsulfonyl)ethyl]-2,3-dihydro-1,3-dioxo-1H-isoindol-4-yl]acetamide (apremilast) The present invention further provides methods of preparing the novel amorphous form of the present invention, as well as an amorphous apremilast obtained by such processes. The present invention is further directed to pharmaceutical compositions comprising the amorphous form of the present invention and a pharmaceutically acceptable carrier and their use in treating and/or preventing disorders ameliorated by the inhibition of TNF-α production or the inhibition of PDE4, e.g., active psoriatic arthritis as well as other chronic inflammatory diseases.

Polymorphs are two or more solid state phases of the same chemical compound that possess different arrangements and/or conformations of the molecules. Polymorphism is the ability of a substance to exist in several different amorphous forms. Different forms of amorphous pharmaceuticals with readily discernible physical and chemical characteristics and some marked differences in their pharmaceutical performance have been reported. Even though amorphous materials do not exhibit long-range periodic atomic ordering, different amorphous phases of the same chemical substance can exhibit significant structural differences in their short-range atomic arrangement. These differences may lead to different physical and chemical properties such as density, stability, processability, dissolution and even bioavailability. Polymorphism in pharmaceuticals is reviewed in Hancock et al. (Journal of Pharmacy and Pharmacology 2002, 54: 1151-1152), the content of which is hereby incorporated by reference. The identification and characterization of various morphic or amorphic forms of a pharmaceutically active compound is of great significance in obtaining medicaments with desired properties including a specific dissolution rate, milling property, bulk density, thermal stability or shelf-life. The novel amorphous form of apremilast disclosed herein possesses improved physicochemical properties including enhanced stability properties.

According to some embodiments, the present invention provides processes for the preparation of amorphous apremilast. According to some embodiments, the apremilast starting material used in such processes may be prepared in accordance with any method known in the art, including, for example, the methods described in WO 2009/120167, WO 2003/080049, WO 2003/080048, and U.S. Pat. No. 6,020, 358. The contents of each of which are hereby incorporated by reference in their entirety.

According to some embodiments, the apremilast starting material is heated until a melt is obtained, preferably under vacuum followed by controlled precipitation by slow/fast cooling.

According to additional embodiments, the apremilast starting material is dissolved in a suitable solvent or a mixture of solvents, preferably THF, acetone or DMF:EtOH=1:3 (v/v) at room temperature. The solvent is then removed by spontaneous evaporation.

According to some embodiments, the apremilast starting material is dissolved in a suitable solvent at room temperature to form an apremilast solution, followed by combining said solution with a suitable anti-solvent to afford the precipitation of amorphous apremilast. In one embodiment, the apremilast solution is added to the anti-solvent. In another embodiment, the anti-solvent is added to the apremilast solution. The anti-solvent is generally used in about a 10 fold excess relative to the solvent. In one currently preferred embodiment, the amorphous apremilast may be further dried under vacuum at a temperature of about 25° C. Suitable solvent-anti-solvent pairs include, but are not limited to, acetone-heptane, heptane-MEK, THF-heptane and water-acetone. Preferred solvents for this method are selected from acetone, MEK and THF. Preferred anti-solvents for this method are selected from water and heptane. Each possibility represents a separate embodiment of the present invention.

According to other embodiments, the apremilast starting material is heated to a temperature of about 120° C. at 5° C./min followed by spontaneous cooling to a temperature of about 25° C. to afford the precipitation of apremilast of the present invention.

According to some embodiments, the invention further provides an amorphous apremilast prepared by each of the processes as described herein.

According to some embodiments, the present invention provides amorphous form of apremilast which is characterized by an X-ray diffraction pattern having a single broad peak expressed between about 10 and about 30 degrees two theta [2θ] as is shown in any of the FIG. 1, 4, 7, 10, 13, 20, 23, 27, 28, 29 or 30. Each possibility represents a separate embodiment of the present invention. According to some embodiments, the amorphous apremilast is further characterized by glass transition temperature and by using various techniques including, but not limited to, thermal analysis (e.g. thermogravimetric analysis (TGA), differential scanning calorimetry (DSC), modulated differential scanning calorimetry (mDSC) and dynamic vapor sorption (DVS)).

Figure 25:
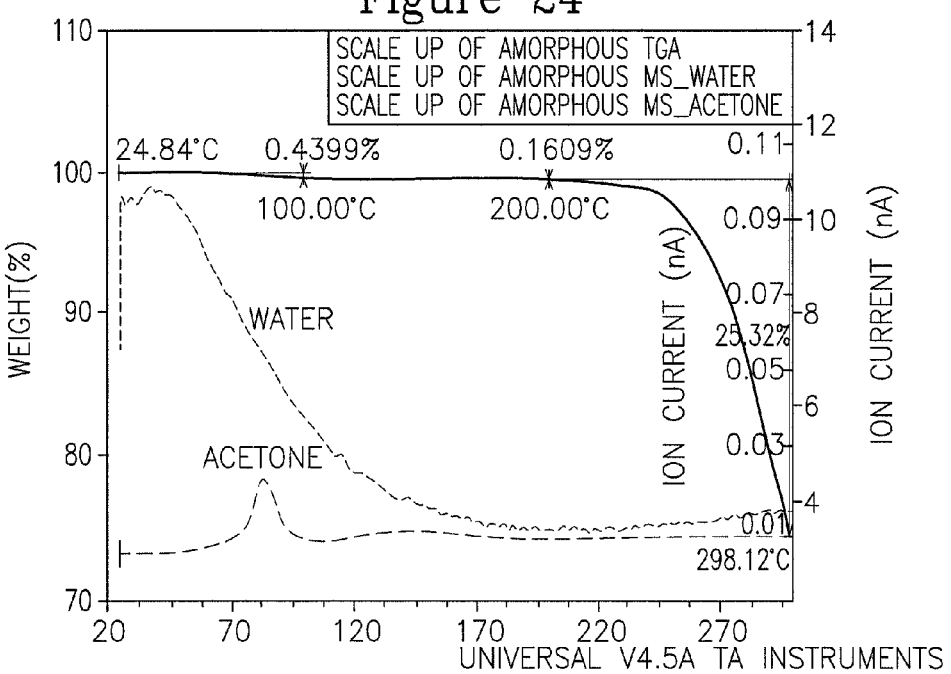
FIG. 25 illustrates a characteristic Thermogravimetric analysis (TGA) profile of an amorphous form of apremilast obtained by scaled-up method III (addition of water to acetone).
Figure 26A:
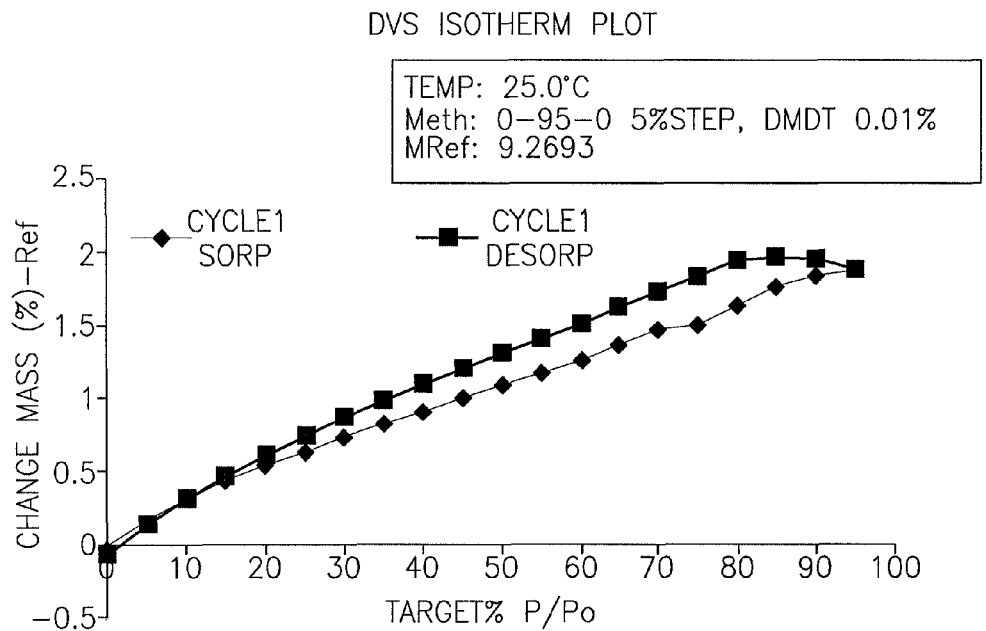
FIG. 26A: DVS isotherm plot. Sorption is represented by diamonds and desorption is represented by squares.
Figure 26B:
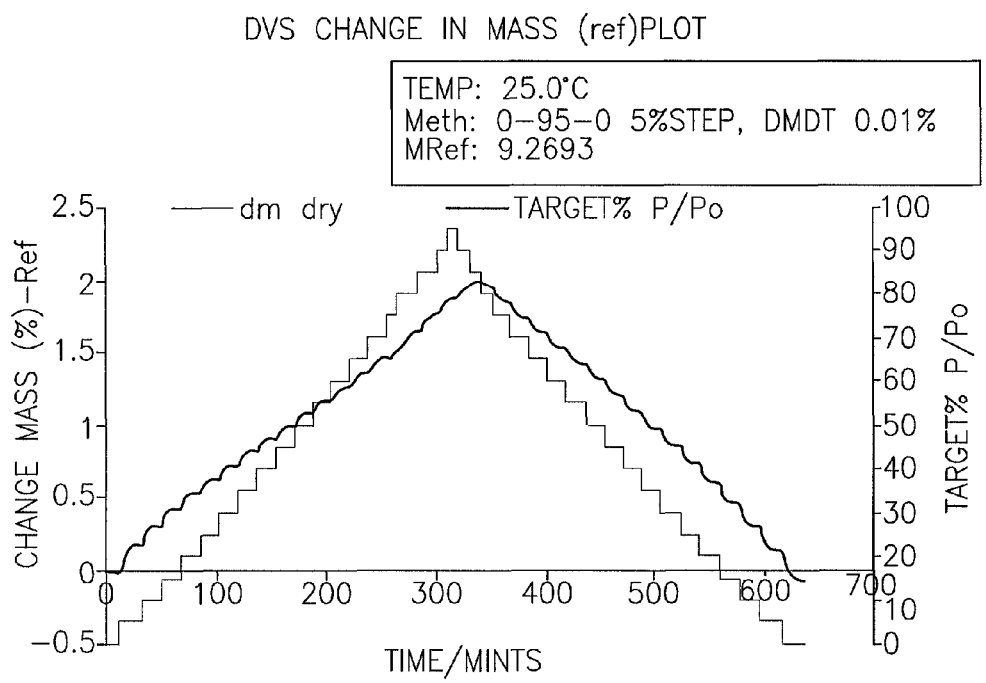
FIG. 26B: DVS change in mass (ref) plot.
Figure 27:
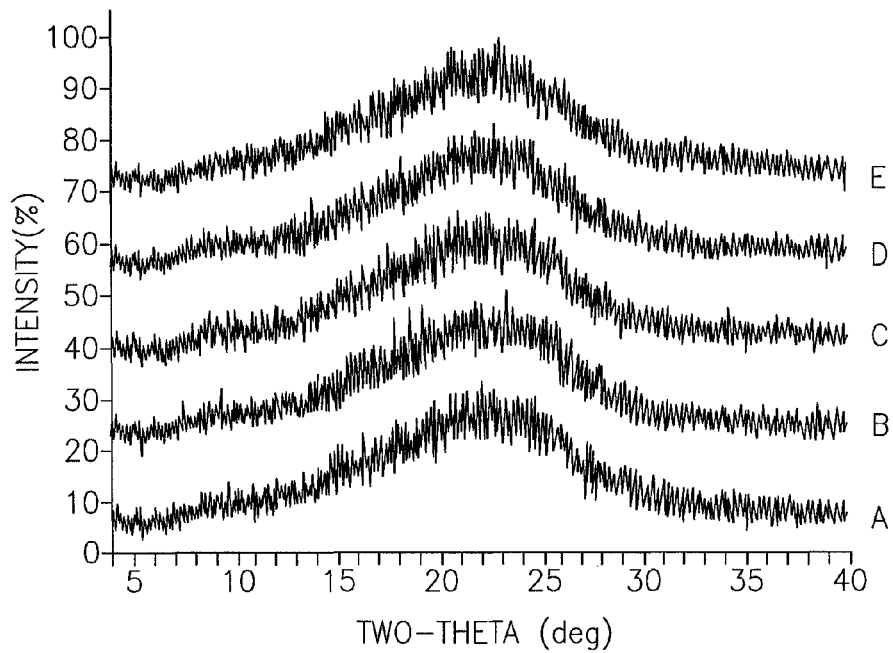
FIG. 27 illustrates a characteristic X-ray diffraction pattern of an amorphous form of apremilast obtained by scaled-up method III (addition of water to acetone). The apremilast was stored at 25° C. in a closed glass vial. Panels A-E represent the following time points: (A) initial time (t=0; control); (B) after one week; (C) after two weeks; (D) after four weeks; and (E) after 3 months.
Figure 28:
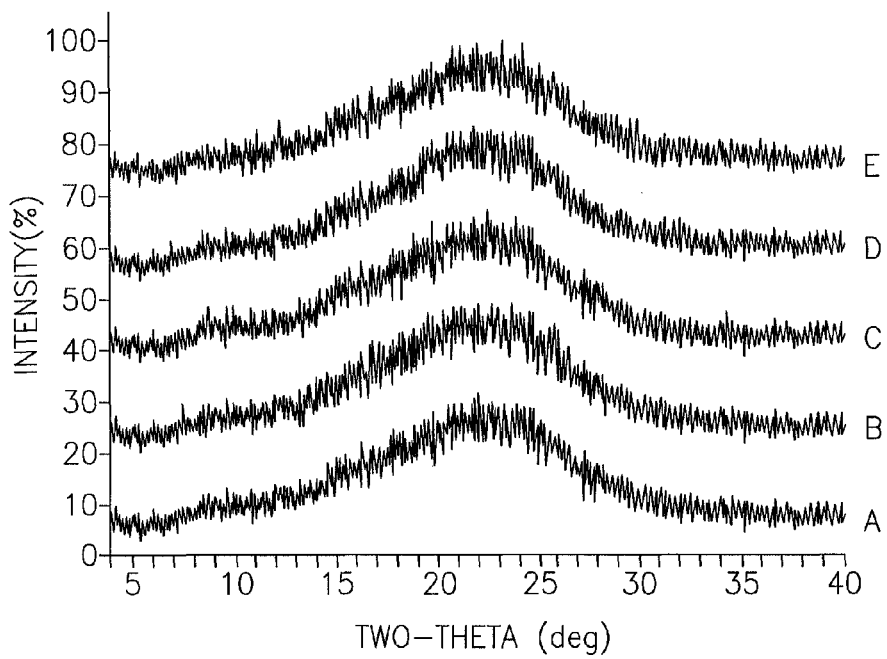
FIG. 28 illustrates a characteristic X-ray diffraction pattern of an anamorphous form of apremilast obtained by scaled-up method III (addition of water to acetone). The apremilast was stored at 25° C./60% RH. Panels A-E represent the following time points: (A) initial time (t=0; control); (B) after one week; (C) after two weeks; (D) after four weeks; and (E) after 3 months.
Figure 29:
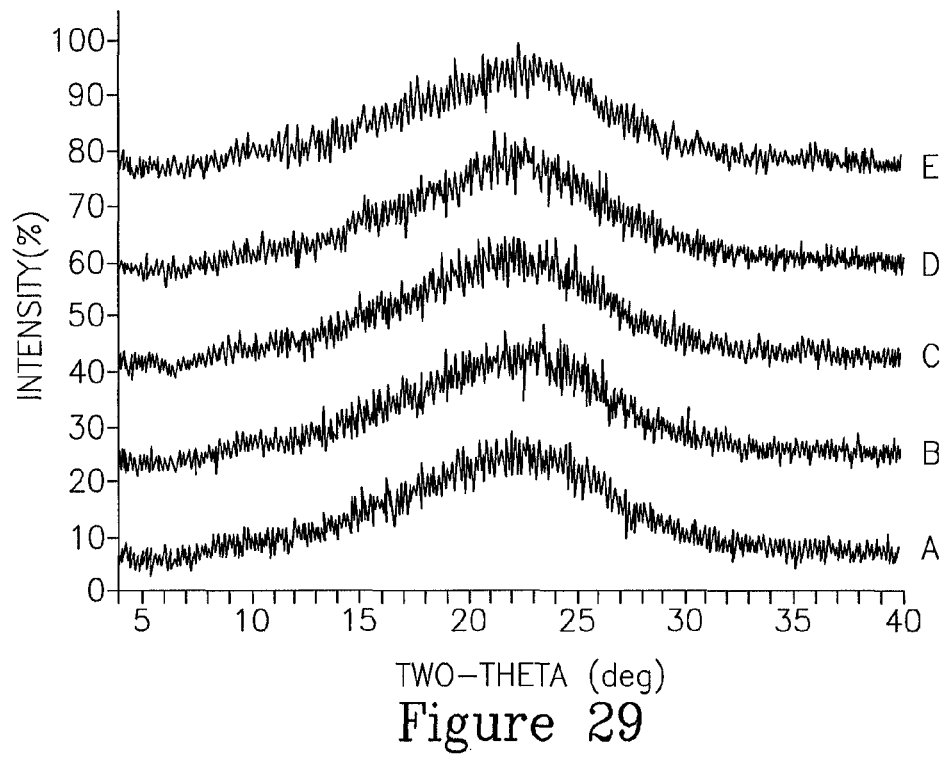
FIG. 29 illustrates a characteristic X-ray diffraction pattern of an amorphous form of apremilast obtained by scaled-up method III (addition of water to acetone). The apremilast was stored at 40° C. in a closed glass vial. Panels A-E represent the following time points: (A) initial time (t=0; control); (B) after one week; (C) after two weeks; (D) after four weeks; and (E) after 3 months.
Figure 35:
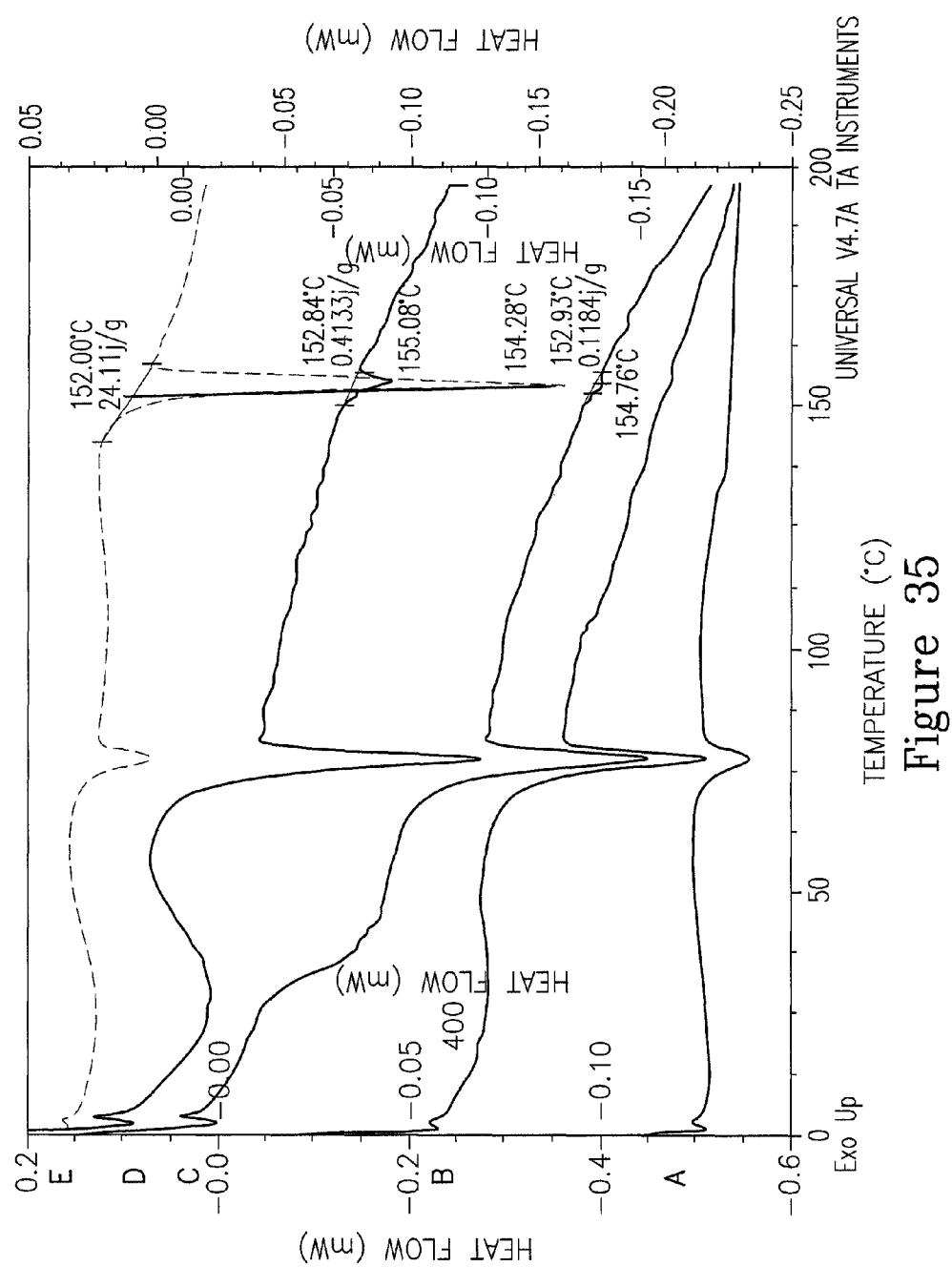
FIG. 35 illustrates a characteristic modulated Differential Scanning calorimetry (mDSC) profile of an amorphous form of apremilast obtained by scaled-up method III (addition of water to acetone). The apremilast was stored at 40° C./75% RH. Panels A-E represent the following time points (A) initial time (t=0; control); (B) after one week; (C) after two weeks; (D) after four weeks; and (E) after 3 months.
Figure 36:
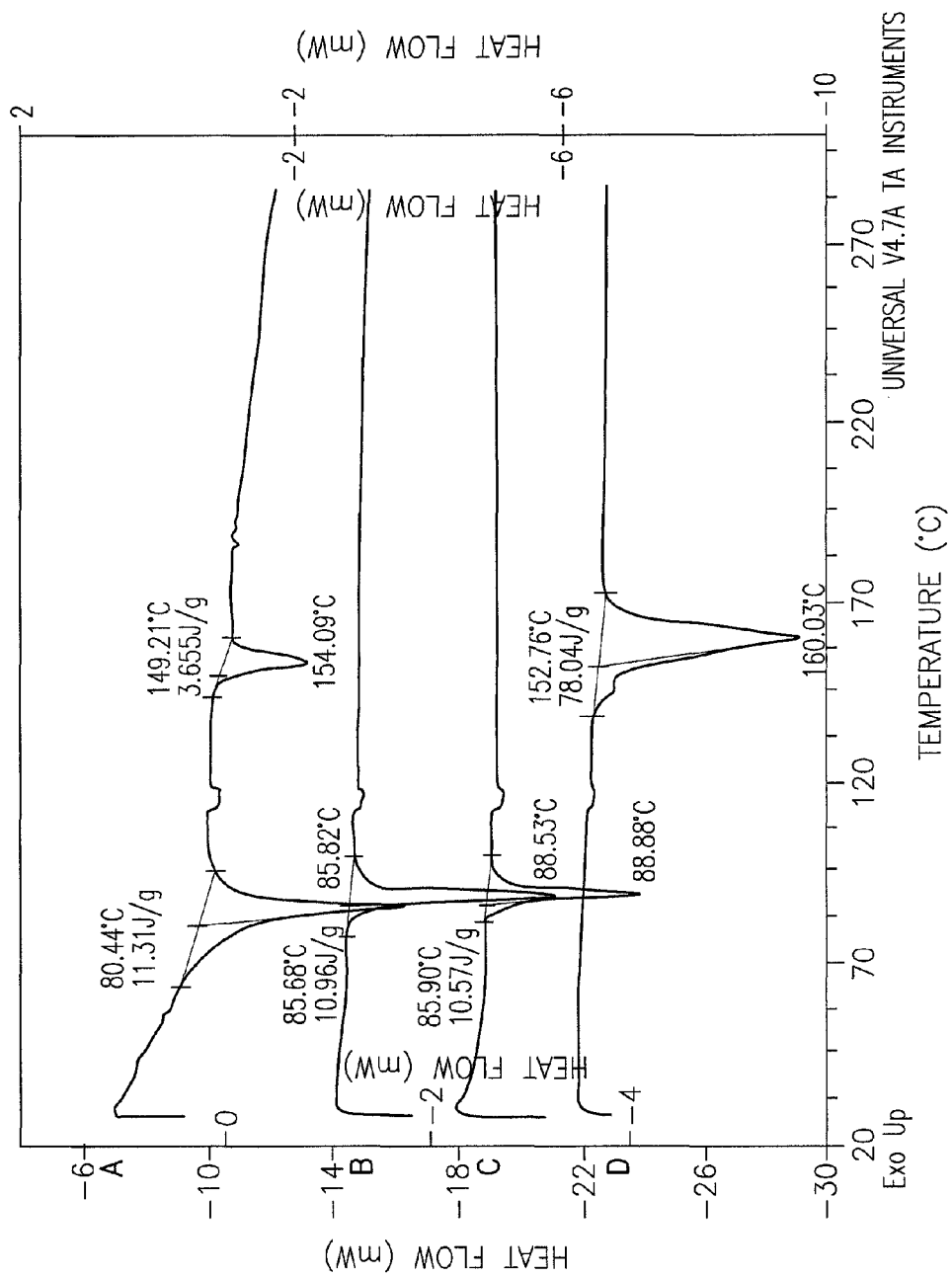
FIG. 36 illustrates a characteristic Differential Scanning calorimetry (DSC) profile at a heating rate of 50° C./min of an amorphous form of apremilast obtained by scaled-up method III (addition of water to acetone). The apremilast was stored at 40° C./75% RH. Panels A-C represent the following time points (A) after two weeks; (B) after four weeks; and (C) after 3 months. Also shown for comparison is the DSC profile of the crystalline apremilast designated as Form B of WO 2009/120167 (panel D).

According to some embodiments, the amorphous apremilast of the present invention is characterized by a modulated DSC profile substantially as shown in any of the FIG. 2, 5, 8, 11A, 11B, 14, 16, 18, 21, 24, 31, 32, 33, 34 or 35, or a DSC profile substantially as shown in FIG. 36. Each possibility represents a separate embodiment of the present invention. According to other embodiments, the amorphous apremilast of the present invention is further characterized by a TGA profile substantially as shown in any of the FIG. 3, 6, 9, 12, 15, 17, 19, 22 or 25. Each possibility represents a separate embodiment of the present invention. According to additional embodiments, the amorphous form has a glass transition temperature between about 36° C. and about 79° C. According to exemplified embodiments, the glass transition temperature of amorphous apremilast is about 36.1° C., 38.0° C., 41.9° C., 44.1° C., 48.2° C., 60.9° C., 75.9° C., 77.2° C., 77.7° C., 78.2° C., or about 133.6° C. In another embodiment, the amorphous apremilast of the present invention is further characterized by a Dynamic Vapor Sorption (DVS) profile substantially as shown in FIGS. 26A and 26B. Each possibility represents a separate embodiment of the present invention.

Therapeutic Uses

The novel amorphous form of the present invention is useful for the treatment of medical conditions mediated by inhibition of PDE4 or inhibition of TNF-α production.

The present invention provides a method of treating medical conditions mediated by PDE4 or TNF-α comprising administering to a subject in need thereof an effective amount of the amorphous form of apremilast as described herein. In some embodiments, the amorphous form of apremilast is administered in a pharmaceutical composition. According to some embodiments, wherein the subject in need is mammal, preferably a human.

According to yet another aspect, the present invention relates to the use of an amorphous form of apremilast as described herein, or a pharmaceutical composition comprising such amorphous apremilast, in the manufacture of a medicament for treating medical condition mediated by PDE4 or TNF-α.

According to some embodiments, the medical condition is selected from the group consisting of psoriasis, psoriatic arthritis, ankylosing spondylitis, Behcet's disease, and rheumatoid arthritis.

Other non-limiting examples of other medical condition mediated by PDE4 (i.e., conditions ameliorated by PDE4 inhibition) include HIV, hepatitis, adult respiratory distress syndrome, bone resorption diseases, chronic obstructive pulmonary diseases, chronic pulmonary inflammatory diseases, dermatitis, inflammatory skin disease, atopic dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft rejection including graft versus host disease, auto immune disease, rheumatoid spondylitis, arthritic conditions (such as rheumatoid arthritis and osteoarthritis), osteoporosis, Crohn's disease, ulcerative colitis, inflammatory bowel disease, multiple sclerosis, systemic lupus erythematosus, erythema nodosum leprosum in leprosy, radiation damage, asthma, and hyperoxic alveolar injury, among others. Each possibility represents a separate embodiment of the invention.

Other non-limiting examples of medical condition mediated by TNF-α (i.e., conditions ameliorated by inhibition of TNF-α production) include psoriasis, psoriatic arthritis, rheumatoid arthritis, chronic cutaneous sarcoid, giant cell arteritis, Parkinson's Disease, prurigo nodularis, lichen planus, complex apthosis, Behcet's Disease, lupus, hepatitis, uveitis, Sjogren's Disease, depression, interstitial cystitis, vulvodynia, prostatitis, osteoarthritis, diffuse large B cell lymphoma, polymyositis dermatomyositis, inclusion body myositis, erosive osteoarthritis, interstitial cystitis, hepatitis, endometriosis, radiculopathy, and pyoderma gangrenosum, among others. Each possibility represents a separate embodiment of the invention.

"A therapeutically effective amount" as used herein refers to an amount of an agent which is effective, upon single or multiple dose administration to the subject in providing a therapeutic benefit to the subject. In additional embodiments, the amorphous apremilast of the present invention is used for the preparation of a medicament.

The present invention further provides the administration of the amorphous apremilast of the present invention in combination therapy with one or more other active ingredients, for example other non-steroidal anti-inflammatory drugs and disease-modifying anti-rheumatic drugs. The combination therapy may include the two or more active ingredients within a single pharmaceutical composition as well as the two or more active ingredients in two separate pharmaceutical compositions administered to the same subject simultaneously or at a time interval determined by a skilled artisan.

Pharmaceutical Compositions

The present invention thus provides pharmaceutical compositions comprising amorphous apremilast and a pharmaceutically acceptable carrier.

The pharmaceuticals can be safely administered orally or non-orally. Routes of administration include, but are not limited to, oral, topical, mucosal, nasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural and sublingual. Each possibility is a separate embodiment of the invention. Preferably, the amorphous apremilast of the present invention is administered orally. The pharmaceutical compositions may be formulated as tablets (including e.g. film-coated tablets, sublingual tablets and orally disintegrating tablets), powders, granules, dragées, pellets, pills, capsules (including soft capsules) and the like. Each possibility is a separate embodiment of the invention.

The term "pharmaceutically acceptable" means approved by a regulatory agency of the Federal or a state government or listed in the U. S. Pharmacopeia or other generally recognized pharmacopeia for use in animals and, more particularly, in humans.

Pharmacologically acceptable carriers that may be used in the context of the present invention include various organic or inorganic carriers including, but not limited to excipients, lubricants, binders, disintegrants, water-soluble polymers and basic inorganic salts. The pharmaceutical compositions of the present invention may further include additives such as, but not limited to, preservatives, anti-oxidants, coloring agents, sweetening agents, souring agents, bubbling agents and flavorings.

Suitable excipients include e.g. lactose, D-mannitol, starch, cornstarch, crystalline cellulose, light silicic anhydride and titanium oxide. Suitable lubricants include e.g. magnesium stearate, sucrose fatty acid esters, polyethylene glycol, talc and stearic acid. Suitable binders include e.g. hydroxypropyl cellulose, hydroxypropyl methyl cellulose, crystalline cellulose, α-starch, polyvinylpyrrolidone, gum arabic powder, gelatin, pullulan and low-substituted hydroxypropyl cellulose. Suitable disintegrants include e.g. cross-linked povidone (any cross-linked 1-ethenyl-2-pyrrolidinone homo-polymer including polyvinylpyrrolidone (PVP) and 1-vinyl-2-pyrrolidinone homo-polymer), cross-linked carmellose sodium, carmellose calcium, carboxymethyl starch sodium, low-substituted hydroxypropyl cellulose, cornstarch and the like. Suitable water-soluble polymers include e.g. cellulose derivatives such as hydroxypropyl cellulose, polyvinylpyrrolidone, hydroxypropyl methyl cellulose, methyl cellulose and carboxymethyl cellulose sodium, sodium polyacrylate, polyvinyl alcohol, sodium alginate, guar gum and the like.

Suitable preservatives include e.g. sodium benzoate, benzoic acid, and sorbic acid. Suitable antioxidants include e.g. sulfites, ascorbic acid and α-tocopherol. Suitable coloring agents include e.g. food colors such as Food Color Yellow No. 5, Food Color Red No. 2 and Food Color Blue No. 2 and the like. Suitable sweetening agents include e.g. dipotassium glycyrrhetinate, aspartame, stevia and thaumatin. Suitable souring agents include e.g. citric acid (citric anhydride), tartaric acid and malic acid. Suitable bubbling agents include e.g. sodium bicarbonate. Suitable flavorings include synthetic substances or naturally occurring substances, including e.g. lemon, lime, orange, menthol and strawberry.

The tablets and other solid dosage forms of the pharmaceutical compositions described herein may optionally be scored or prepared with coatings and shells, such as enteric coatings and other coatings well known in the art. They may also be formulated so as to provide slow or controlled release of the active ingredient therein using, for example, hydroxypropyl methyl cellulose in varying proportions to provide the desired release profile, other polymer matrices and the like. The active ingredient may also be in microencapsulated form, if appropriate, with one or more of the above-described excipients.

The tablets and other solid dosage forms may be made by compression or molding, optionally with one or more excipients as is known in the art. For example, molded tablets may be made by molding in a suitable machine a mixture of the powdered active ingredient moistened with an inert liquid diluent.

The principles of the present invention are demonstrated by means of the following non-limiting examples.

EXAMPLES

Example 1: General Preparation Methods of Apremilast Amorphous

1. Reagents

Ethanol, HPLC grade, Sigma-Aldrich, Lot No. SHBC4338V
Acetone, HPLC grade, Sinopharm Chemical Reagent Co. Ltd, Lot No. 20121012
THF, HPLC grade, Sigma-Aldrich, Lot No. 18896BPV
Methyl ethyl ketone (MEK), AR, Shanghai Runjie Chemical Reagent Co. Ltd., Lot No. 20110105
Heptane, HPLC grade, TEDIA Co., INC., Lot No. HS1712-001
DMF, AR, Shanghai Runjie Chemical Reagent Co. Ltd., Lot No. 20110601

2. Instruments

Milli-Q Direct 8 Water Purification Equipment
Sartorius CP 225D Balance
Mettler-Toledo XP6 Balance
Eppendorf thermomixer comfort
Rigaku D/MAX 2200 X-ray powder diffractometer (XRPD)
Nikon LV100 Polarized Light Microscopy (PLM)
TA Q2000 Differential Scanning calorimetry (DSC)
TA Q5000 IR Thermal Gravimetric Analysis (TGA)/ Hiden Quantitive Gas Analysis (QGA)
Dynamic Vapor Sorption (DVS) Advantage 1

3. XRPD, mDSC, DSC, DVS and TGA Methods 3.1 XRPD Method

Details of XRPD method used in the tests are mentioned below:

X-ray Generator: Cu, Kα ($\lambda$=1.54179 Å).
Tube Voltage: 40 kV; Current: 40 mA.
Scanning Scope: 4 to 40 deg;
Sample rotation speed: 15 rpm.
Scanning rate: 10 deg/min 3.2 Modulated Differential Scanning Calorimetry (mDSC)

Details of mDSC methods used in the tests are mentioned below:

Method I: Amorphous samples (about 1 mg) were run a modulated DSC using Tzero aluminum pans heated from 0° C. to 200° C. at speed of 2° C./min, with modulation temperature amplitude 1.0° C. and modulation 60 s.

Method II: The two-cycle heating mDSC was run using Tzero aluminum hermetic pans with pinhole with first cycle heated from 0° C. to 160° C. at speed of 2° C./min and the second cycle from 0° C. to 260° C. at speed of 2° C./min.

3.3 Differential Scanning Calorimetry (DSC)

Details of DSC method used in the tests are mentioned below:

Samples (about 0.5 mg) were run using Tzero aluminum pans heated from 25° C. to 300° C. at speed of 10° C./min or 50° C./min (for amorphous sample at 40° C./75% RH at the third month).

3.4 Thermal Gravimetric Analysis (TGA)

Details of TGA method used in the tests are mentioned below:

Samples (about 1-3 mg) were placed in an open platinum pan and heated from room temperature to 250° C.-300° C. at a rate of 10° C./min.

3.5 Dynamic Vapor Sorption (DVS)

Details of DVS method used in the tests are mentioned below:

Samples (about 10 mg) were transferred into a DVS pan, the weight changes were recorded with respect to the atmospheric humidity at 25° C.

The following parameters were used:

Equilibrium: dm/dt: 0.01%/min. (for min: 10 min and max: 180 min).
Drying: 0% RH for 120 min.
RH (%) measurement step: 5%,
RH (%) measurement step scope: 0~95~0%.

| Hygroscopicity Classification | Water Sorption Criterion* |
|---|---|
| Deliquescent | Sufficient water is absorbed to form a liquid |
| Very hygroscopic | ΔW % ≥ 15% |
| Hygroscopic | 15% > ΔW % ≥ 2% |
| Slightly hygroscopic | 2% > ΔW % ≥ 0.2% |
| Non-hygroscopic | ΔW % < 0.2% |

*At 25 ± 1° C. and 80 ± 2% RH (European Pharmacopoeia 6.0)

4. General Preparation Methods 4.1 Method I: Slow Precipitation from Solutions

Apremilast (Form I, equivalent to form B of WO2009/120167) was dissolved in a solvent or a mixture of solvents at room temperature. The solvents were then evaporated spontaneously to obtain amorphous form.

4.2 Method II: Solid Thermal Heating/Cooling Experiments

Apremilast (Form I) was heated to melt under vacuum followed by controlled precipitation of the melted compound by fast/slow cooling.

4.3 Method III: Solvent-Anti-Solvent Precipitation

Apremilast (Form I) was dissolved in a solvent at room temperature and filtered. Anti-solvent (10 fold volume) was quickly added and stirred into the apremilast solution or the apremilast solution was quickly added and stirred into anti-solvent (10 fold volume). Once the precipitant formed, it was centrifuged at 10,000 rpm for 2 minutes. In a scaled up procedure (using 5 g of apremilast), once the precipitant formed, the solid was filtered and then dried in a vacuum drier at 25° C.

4.4 Method IV: Drying of Solvates/Hydrates

Apremilast Form II (equivalent to form D of WO2009/120167) was heated to 120° C. at 5° C./min and kept for 5 min, then cooled spontaneously to room temperature.

Example 2: Amorphous Apremilast (Method I)

General method I was performed. Thus, apremilast (Form I) was dissolved in the following solvents or solvent mixtures: THF, acetone and DMF:EtOH=1:3 (v/v) at room temperature. The solvents were then evaporated spontaneously to obtain a solid amorphous form of apremilast.

Figure 2:
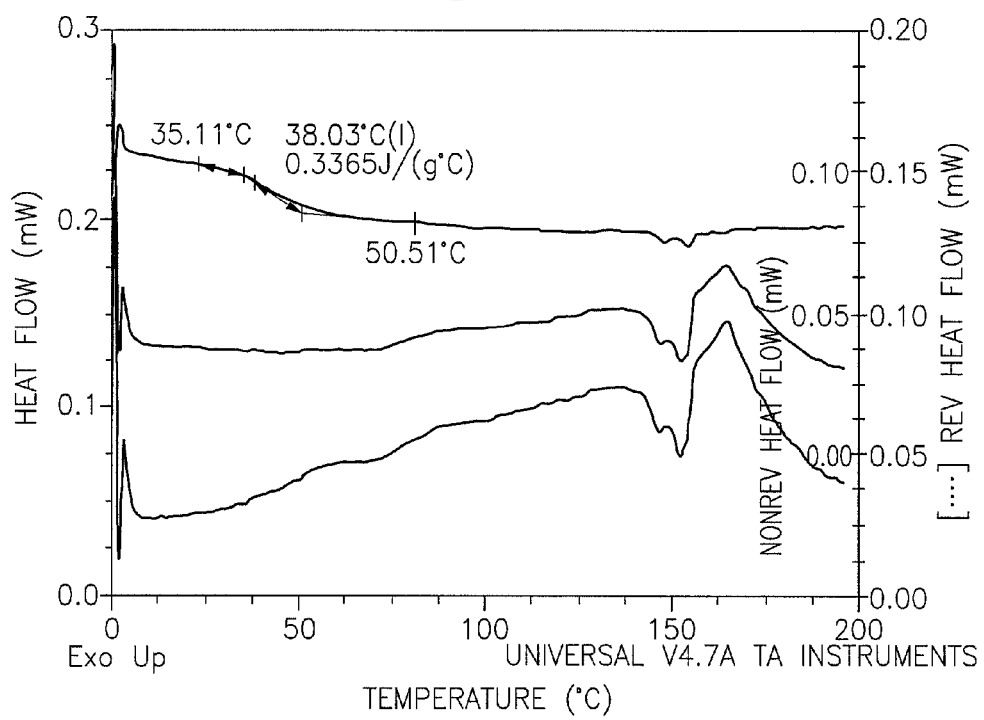
FIG. 2 illustrates a characteristic modulated Differential Scanning calorimetry (mDSC) profile of an amorphous form of apremilast obtained by method I (in THF).
Figure 3:
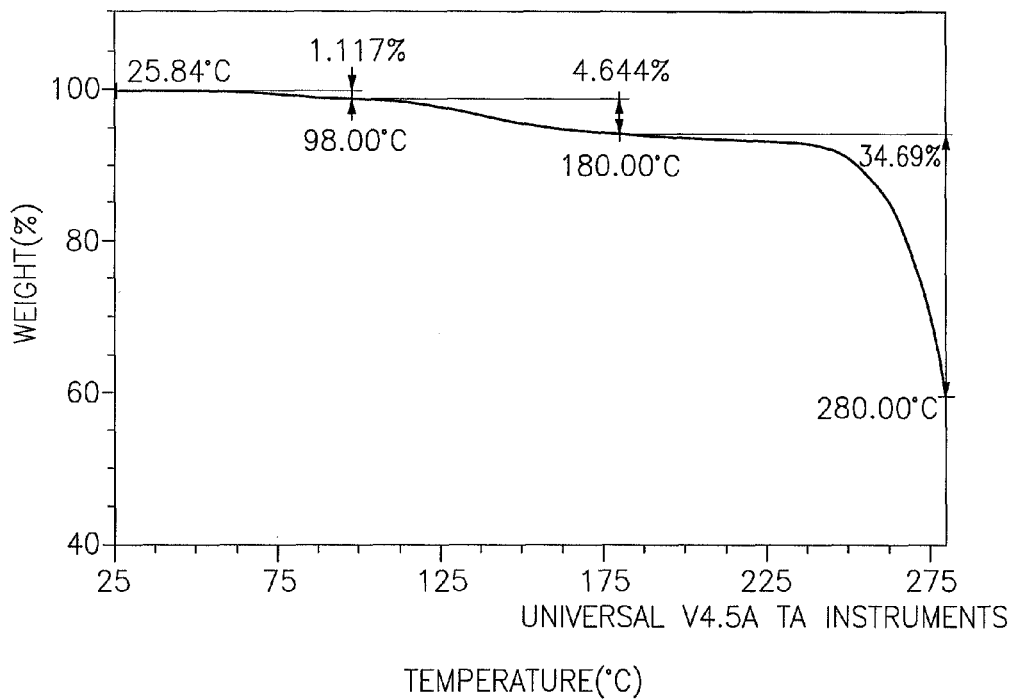
FIG. 3 illustrates a characteristic Thermogravimetric analysis (TGA) profile of an amorphous form of apremilast obtained by method I (in THF).

FIG. 1 shows a characteristic XRPD of the amorphous form obtained by this method using THF as the solvent. FIG. 2 illustrates a characteristic modulated DSC. The glass transition temperature of the amorphous form obtained by this method is 38.0° C. FIG. 3 illustrates a characteristic TGA profile with a weight loss of about 1.12% between about 25° C. and about 98° C. and a weight loss of about 4.64% between about 98° C. and about 180° C.

Figure 4:
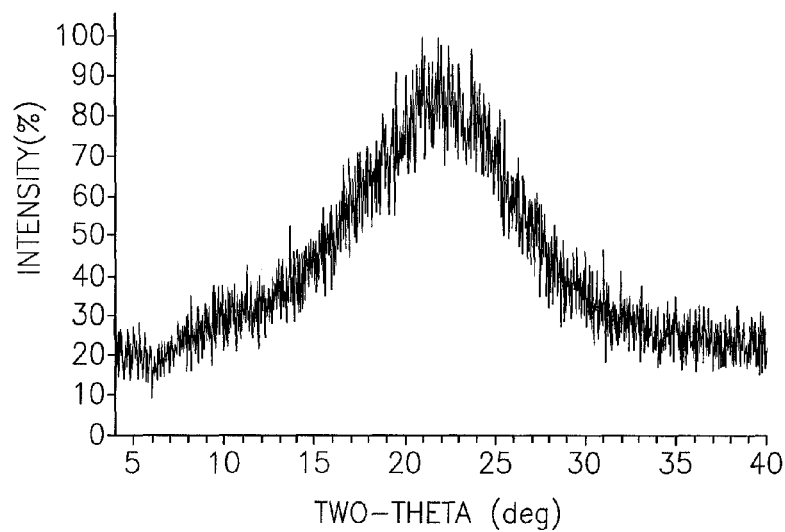
FIG. 4 illustrates a characteristic X-ray diffraction pattern of an amorphous form of apremilast obtained by method I (in acetone).
Figure 5:
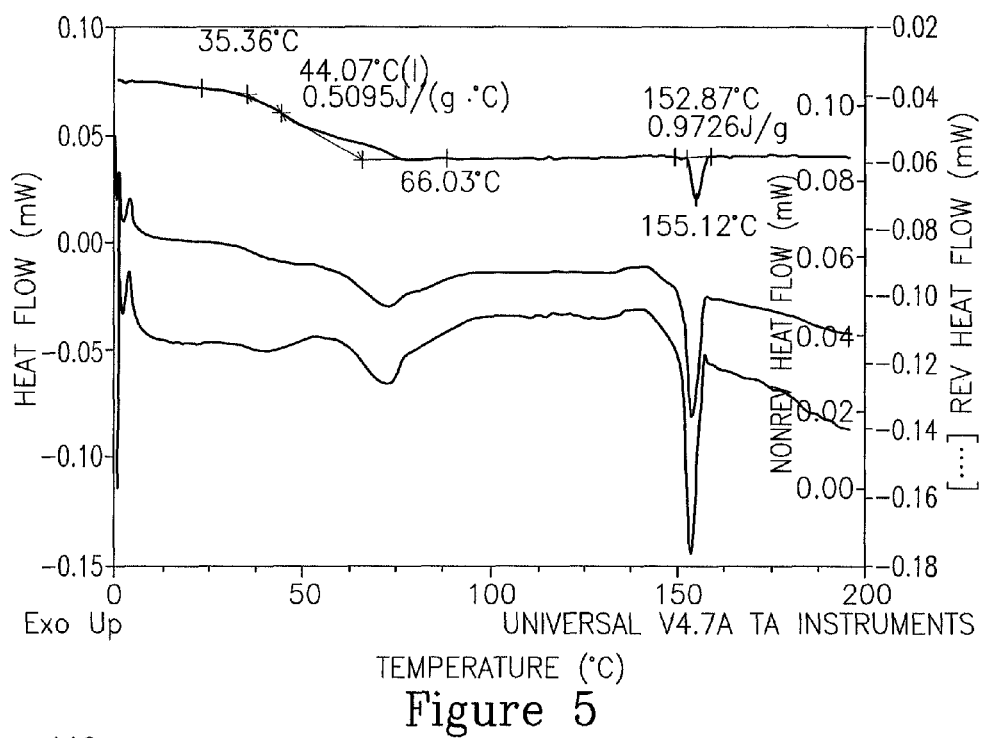
FIG. 5 illustrates a characteristic modulated Differential Scanning calorimetry (mDSC) profile of an amorphous form of apremilast obtained by method I (in acetone).
Figure 6:
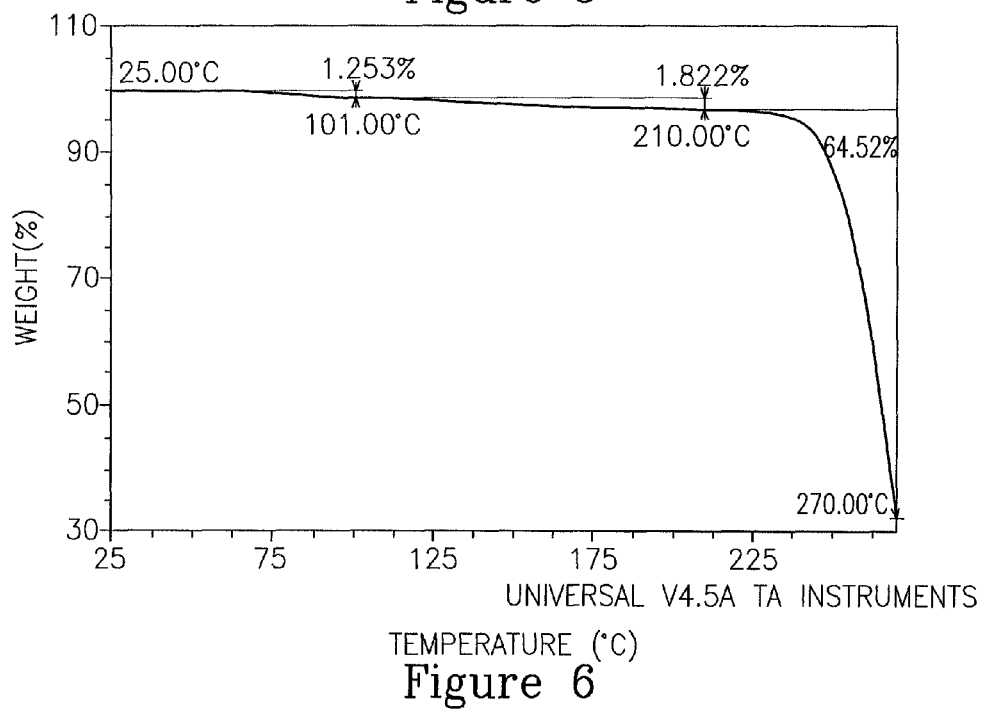
FIG. 6 illustrates a characteristic Thermogravimetric analysis (TGA) profile of an amorphous form of apremilast obtained by method I (in acetone).

FIG. 4 shows a characteristic XRPD of the amorphous form obtained by this method using acetone as a solvent. FIG. 5 illustrates a characteristic modulated DSC profile. The glass transition temperature of the amorphous form obtained by this method is 44.1° C. FIG. 6 illustrates a characteristic TGA profile with a weight loss of about 1.25% between about 25° C. and about 101° C., and a weight loss of about 1.82% between about 101° C. and about 210° C.

Figure 7:
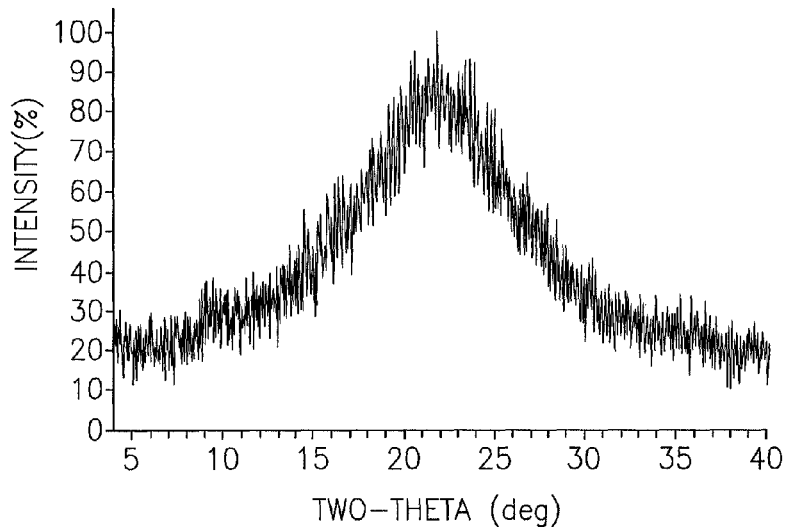
FIG. 7 illustrates a characteristic X-ray diffraction pattern of an amorphous form of apremilast obtained by method I (in DMF:EtOH=1:3 (v/v)).
Figure 8:
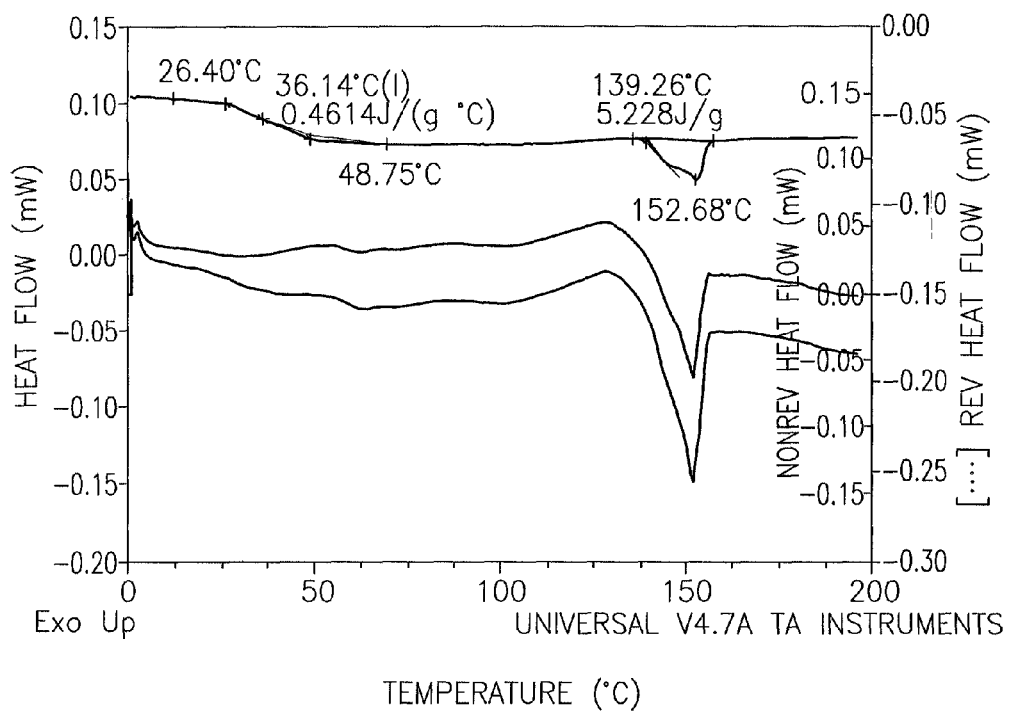
FIG. 8 illustrates a characteristic modulated Differential Scanning calorimetry (mDSC) profile of an amorphous form of apremilast obtained by method I (in DMF:EtOH=1:3 (v/v)).
Figure 9:
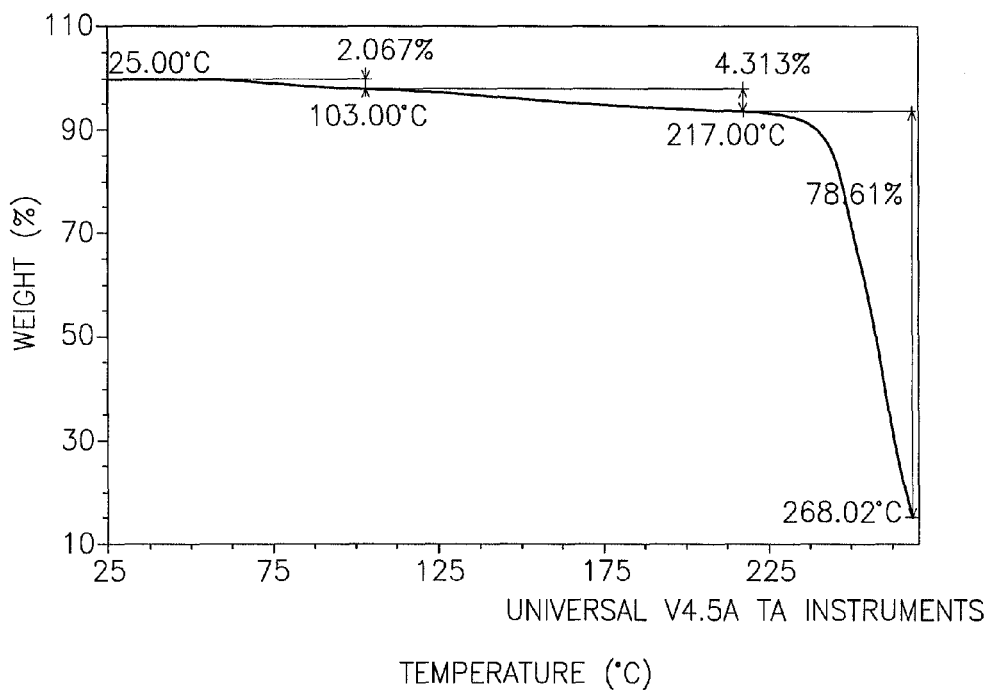
FIG. 9 illustrates a characteristic Thermogravimetric analysis (TGA) profile of an amorphous form of apremilast obtained by method I (in DMF:EtOH=1:3 (v/v)).

FIG. 7 shows a characteristic XRPD of the amorphous form obtained by this method using DMF:EtOH=1:3 (v/v) as a solvent mixture. FIG. 8 illustrates a characteristic modulated DSC profile. The glass transition temperature of the amorphous form obtained by this method is 36.1° C. FIG. 9 illustrates a characteristic TGA profile with a weight loss of about 2.07% between about 25° C. and about 103° C., and a weight loss of about 4.31% between about 103° C. and about 217° C.

Example 3: Amorphous Apremilast (Method II)

Figure 10:
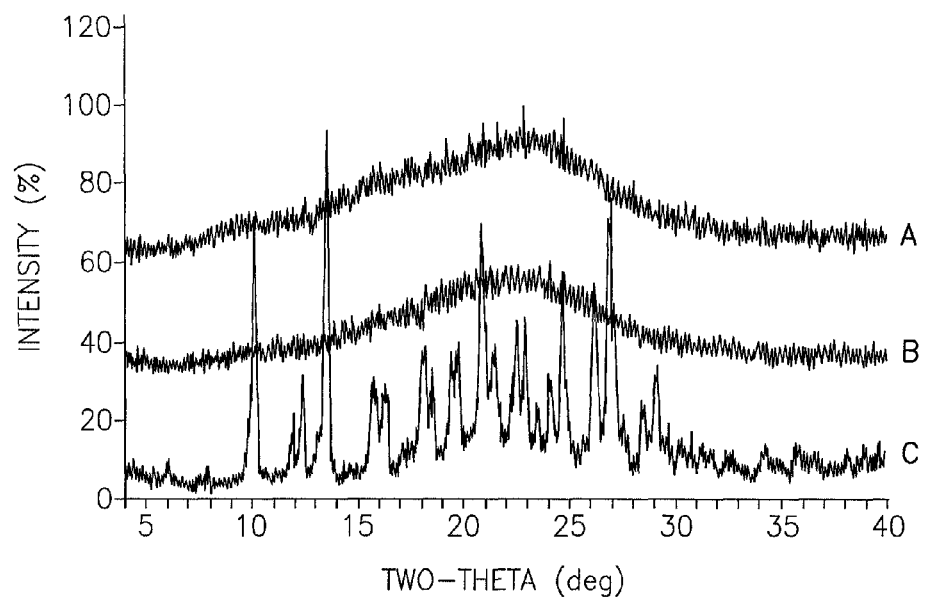
FIG. 10 illustrates a characteristic X-ray diffraction pattern of an amorphous form of apremilast obtained by method II (panel A-B; slow and fast cooling). Also shown for comparison is the X-ray diffraction pattern of crystalline apremilast designated as From B in WO 2009/120167 (panel C).
Figure 11A:
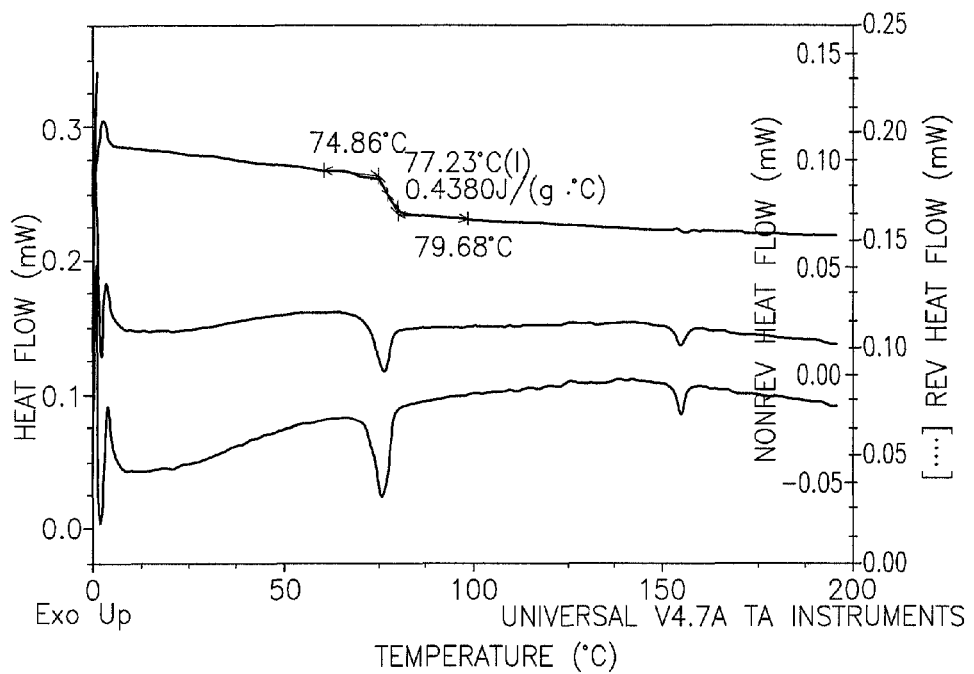
FIG. 11A: mDSC profile of an amorphous apremilast obtained by slow cooling.
Figure 11B:
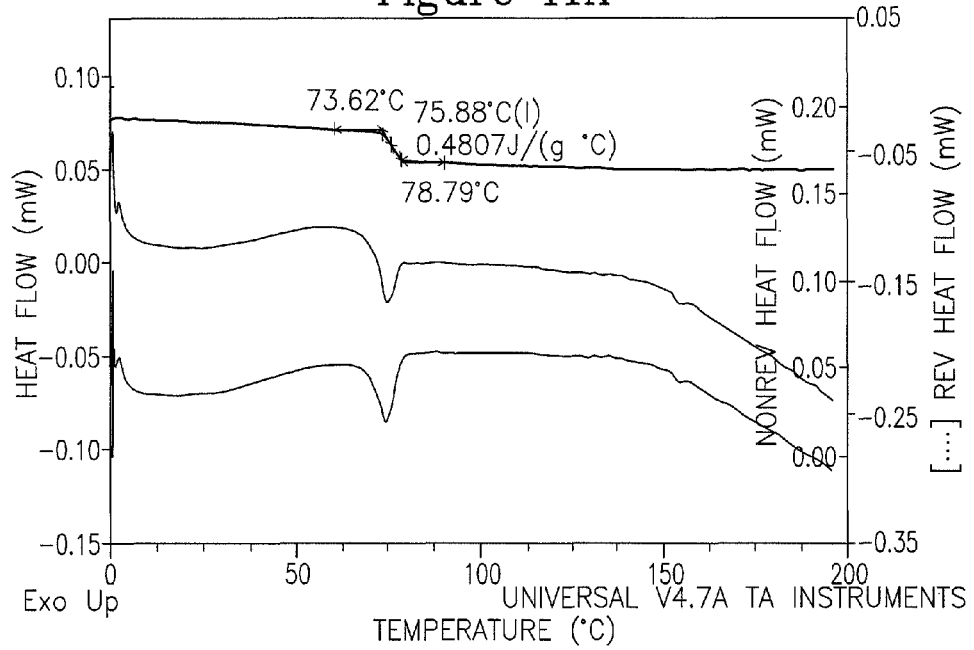
FIG. 11B: mDSC profile of an amorphous apremilast obtained by fast cooling.
Figure 12:
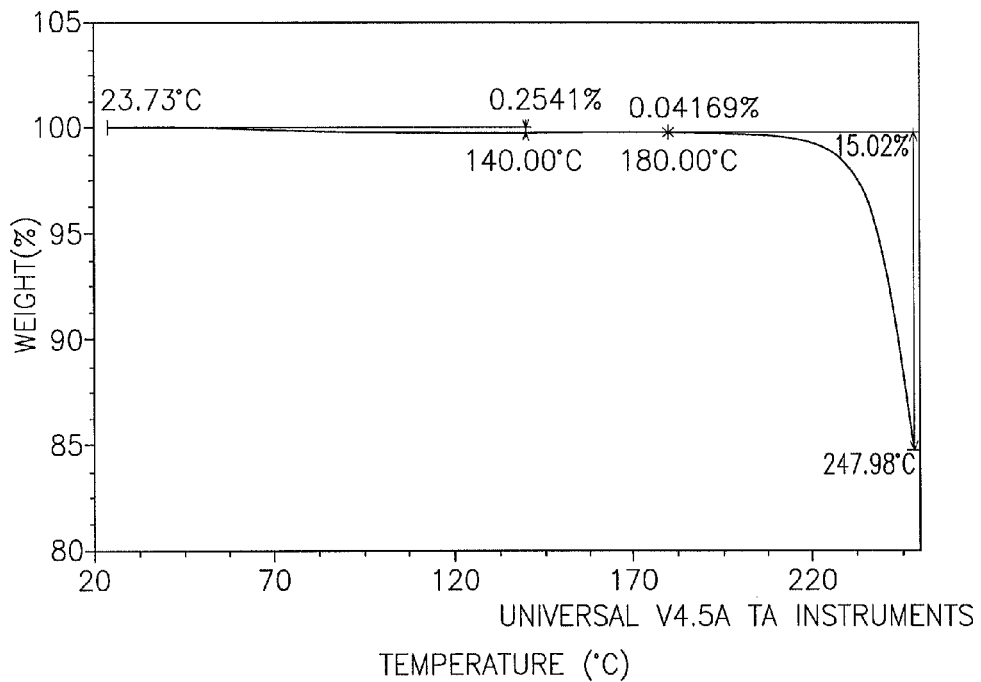
FIG. 12 illustrates a characteristic Thermogravimetric analysis (TGA) profile of an amorphous form of apremilast obtained by method II (slow cooling).

General method II was performed. Thus, apremilast (form I) was heated to melt under vacuum followed by controlled precipitation of the melted compound by fast/slow cooling. FIG. 10 (panel A-B) illustrates a broad X-ray diffraction peak with both conditions (fast and slow cooling), characteristic of an amorphous powder. Also shown in FIG. 10 (panel C), for comparison, is the X-ray diffraction pattern of crystalline apremilast Form I. The amorphous form obtained by slow or fast cooling was further characterized by modulated DSC (FIGS. 11A and 11B). The glass transition temperatures of the amorphous form obtained by the slow cooling method is 77.2° C. and 75.9° C. by the fast cooling method. FIG. 12 illustrates a characteristic TGA profile of amorphous apremilast obtained by the slow cooling method, with a weight loss of about 0.29% between about 24° C. and about 180° C.

Example 4: Amorphous Apremilast (Method III)

Figure 13:
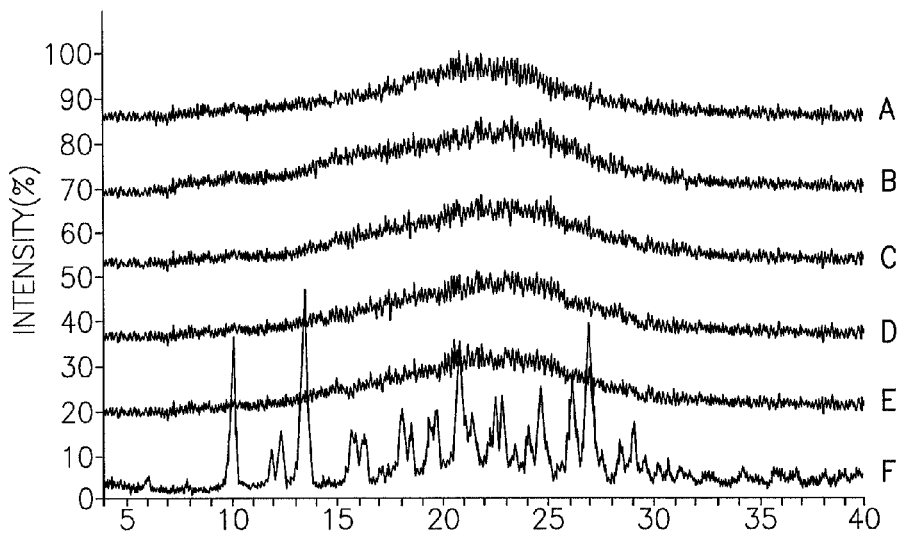
FIG. 13 illustrates a characteristic X-ray diffraction pattern of an amorphous form of apremilast obtained by method III. Panels A-E represent the following solvent-anti-solvent systems: addition of (A) THF to heptane; (B) water to acetone; (C) heptane to MEK; (D) acetone to heptane; and (E) heptane to acetone. Also shown for comparison is the X-ray diffraction pattern of crystalline apremilast designated as Form B in WO 2009/120167 (panel F).

General method III was performed. Thus, about 50 mg apremilast (Form I) was dissolved in a solvent at room temperature and then filtered into clean vials to afford a clear solution. Then an anti-solvent (10 fold volume) was quickly added and stirred into the clear apremilast solution, or the clear apremilast solution was quickly added and stirred into anti-solvent. Heptane and water were used as exemplary anti-solvents for these experiments, while acetone, MEK and THF were used as exemplary solvents. Once the precipitant formed, it was centrifuged at 10,000 rpm for 2 minutes. FIG. 13 panels (A) to (E) shows the characteristic XRPD profiles of the amorphous form obtained by this method using various solvent systems. Also shown in FIG. 13 panel (F) for comparison, is the X-ray diffraction pattern of crystalline apremilast Form I.

Figure 14:
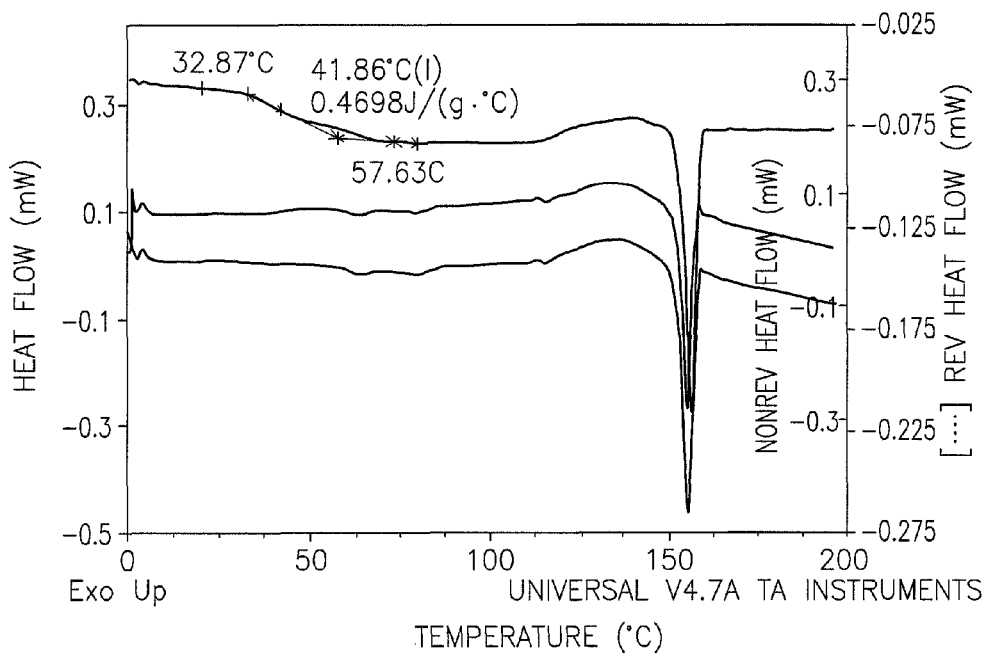
FIG. 14 illustrates a characteristic modulated Differential Scanning calorimetry (mDSC) profile of an amorphous form of apremilast obtained by method III (addition of acetone to heptane).
Figure 15:
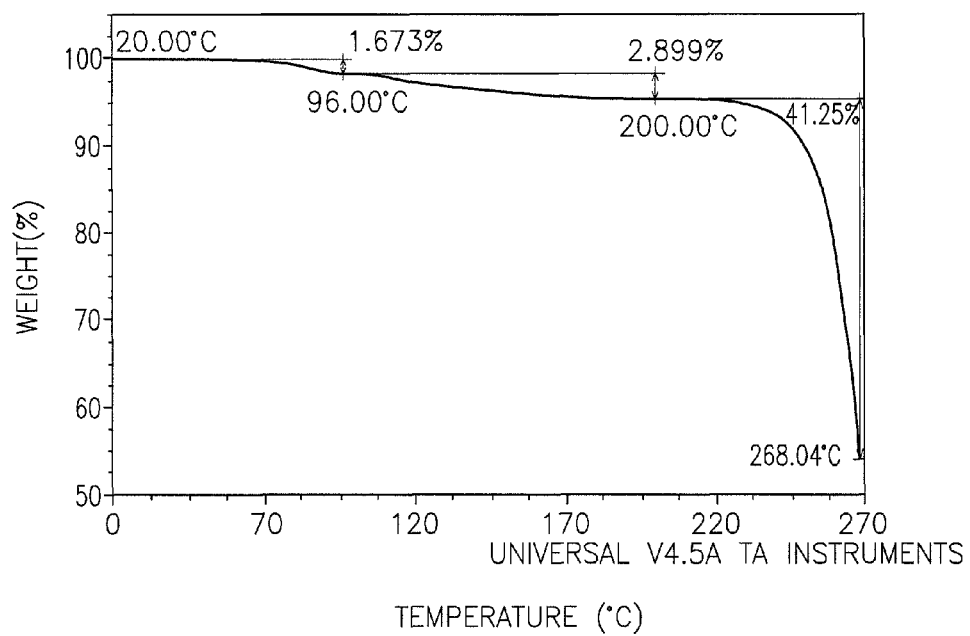
FIG. 15 illustrates a characteristic Thermogravimetric analysis (TGA) profile of an amorphous form of apremilast obtained by method III (addition of acetone to heptane).

FIG. 13 panel (D) shows characteristic XRPD of the amorphous form obtained by addition of acetone to heptane. FIG. 14 illustrates a characteristic modulated DSC. The glass transition temperature of the amorphous form obtained by this method is 41.9° C. FIG. 15 illustrates a characteristic TGA profile with a weight loss of about 1.67% between about 20° C. and about 96° C. and a weight loss of about 2.90% between about 96° C. and about 200° C.

Figure 16:
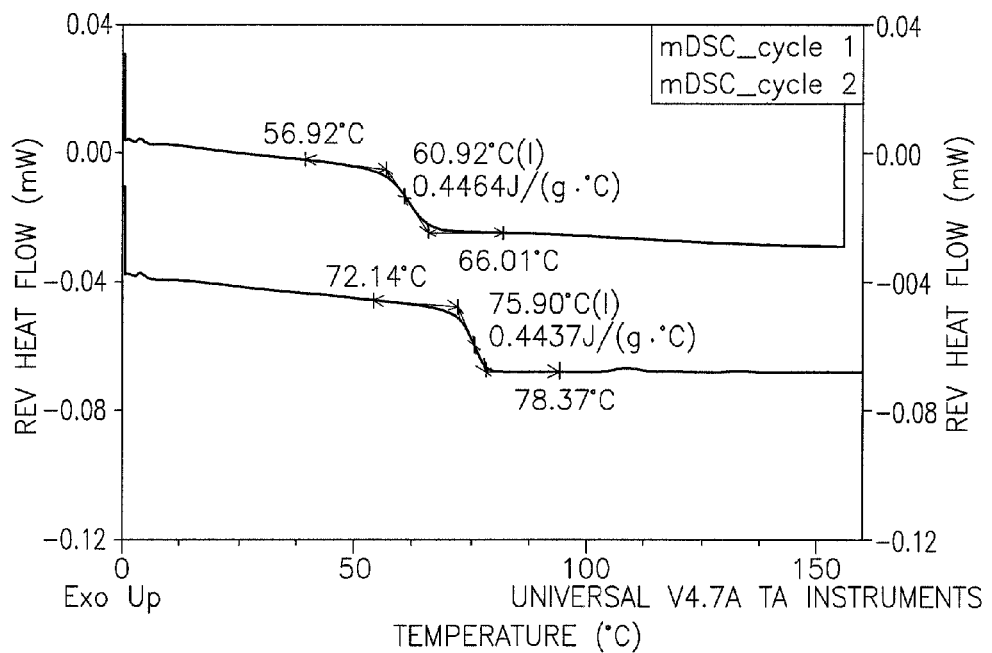
FIG. 16 illustrates a characteristic modulated Differential Scanning calorimetry (mDSC) profile of an amorphous form of apremilast obtained by method III (addition of THF to heptane).
Figure 17:
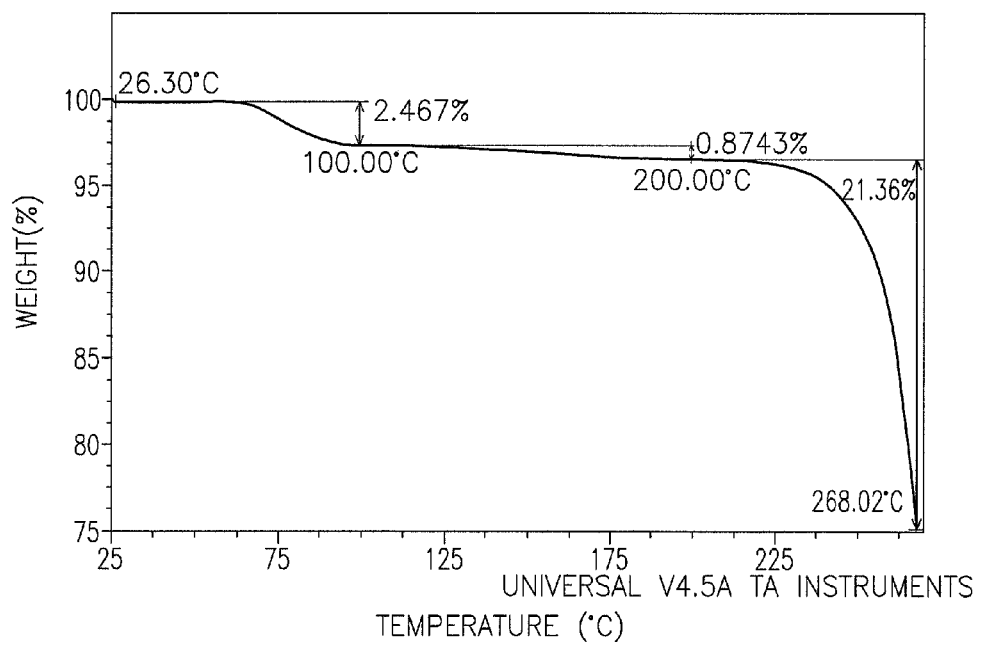
FIG. 17 illustrates a characteristic Thermogravimetric analysis (TGA) profile of an amorphous form of apremilast obtained by method III (addition of THF to heptane).

FIG. 13 panel (A) shows characteristic XRPD of the amorphous form obtained by addition of THF to heptane. FIG. 16 illustrates a characteristic modulated DSC profile. The glass transition temperature of the amorphous form obtained by this method is 60.9° C., based on the first heating cycle. FIG. 17 illustrates a characteristic TGA profile with a weight loss of about 2.47% between about 26.3° C. and about 100° C., and a weight loss of about 0.87% between about 100° C. and about 200° C.

Figure 18:
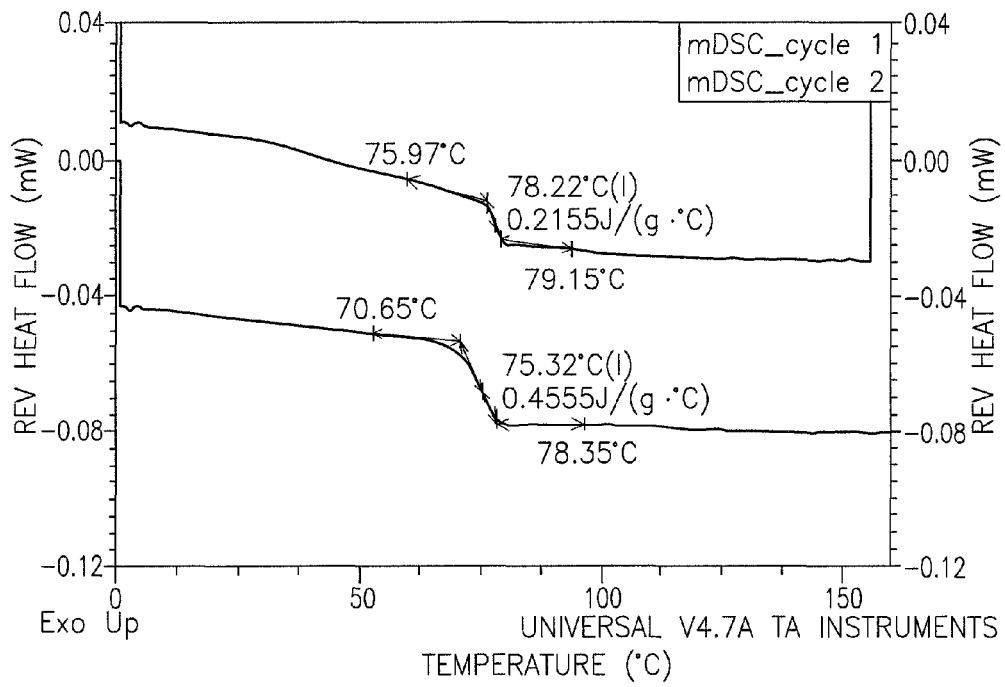
FIG. 18 illustrates a characteristic modulated Differential Scanning calorimetry (mDSC) profile of an amorphous form of apremilast obtained by method III (addition of water to acetone).
Figure 19:
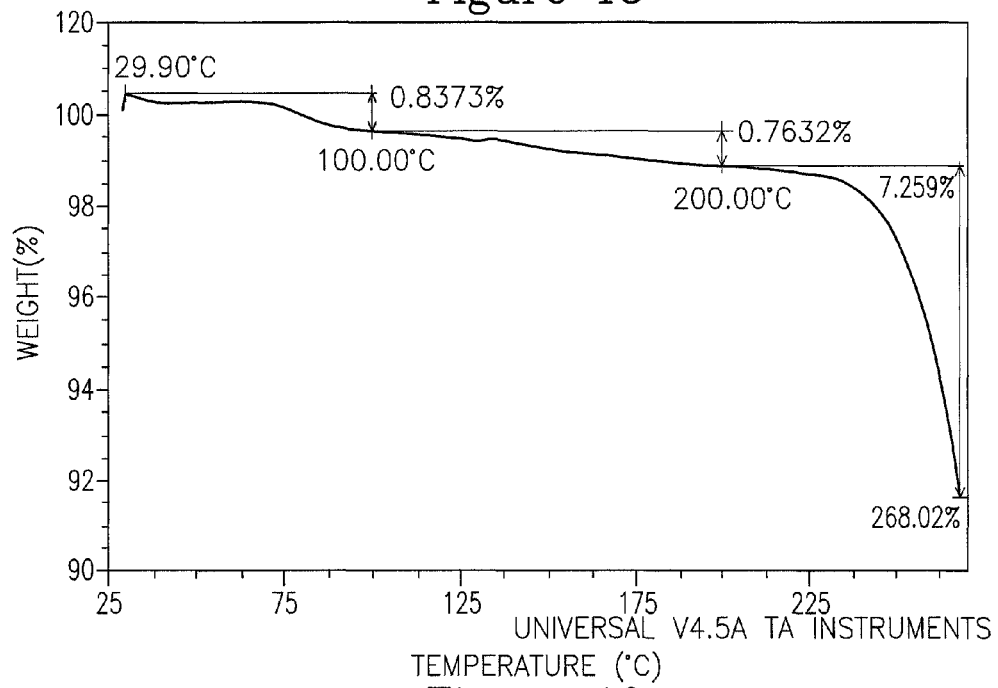
FIG. 19 illustrates a characteristic Thermogravimetric analysis (TGA) profile of an amorphous form of apremilast obtained by method III (addition of water to acetone).

FIG. 13 panel (B) shows characteristic XRPD of the amorphous form obtained by addition of water to acetone. FIG. 18 illustrates a characteristic modulated DSC profile. The glass transition temperature of the amorphous form obtained by this method is 78.2° C., based on the first heating cycle. FIG. 19 illustrates a characteristic TGA profile with a weight loss of about 0.84% between about 29.9° C. and about 100° C., and a weight loss of about 0.76% between about 100° C. and about 200° C.

FIG. 13 panel (C) shows characteristic XRPD of the amorphous form obtained by addition of heptane to MEK.

FIG. 13 panel (E) shows characteristic XRPD of the amorphous form obtained by addition of heptane to acetone.

The results demonstrate that the, amorphous form obtained by adding water to acetone showed relatively higher glass transition temperature (78.2° C.) than that obtained, for example by adding THF to heptane (60.9° C.). The weight loss from TGA results also showed that the amorphous form obtained by adding water to acetone contained relatively less residual solvent or water than the others. Hence, the amorphous form of apremilast obtained via precipitation from water and acetone represents a currently preferred embodiment of the present invention.

Example 5: Amorphous Apremilast (Method IV)

General method IV was performed. Thus, apremilast Form II was heated to 120° C. at 5° C./min and kept for 5 min, then cooled spontaneously to room temperature.

Figure 20:
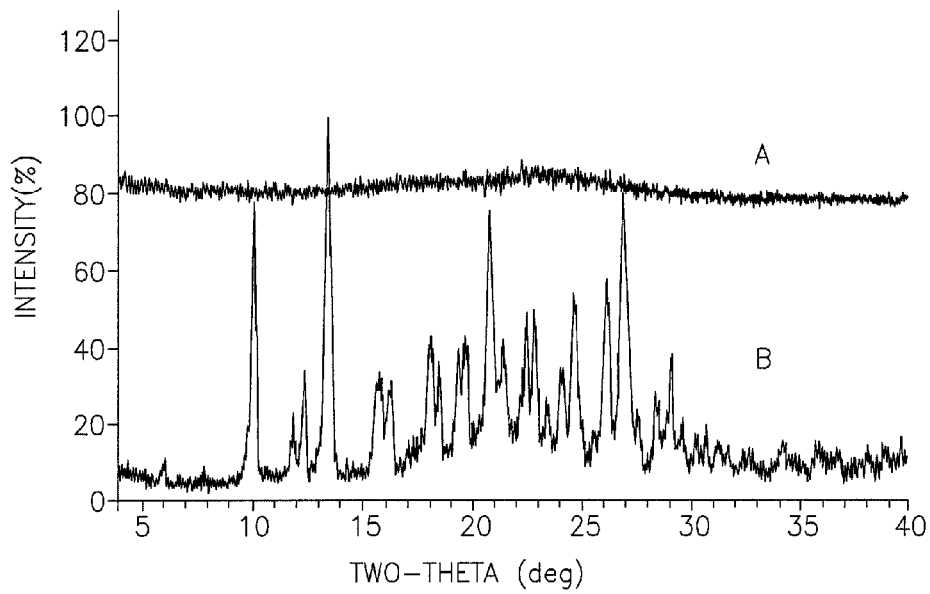
FIG. 20 illustrates a characteristic X-ray diffraction pattern of an amorphous form of apremilast obtained by method IV (panel A). Also shown for comparison is the X-ray diffraction pattern of the crystalline apremilast designated as Form B of WO 2009/120167 (panel B).
Figure 21:
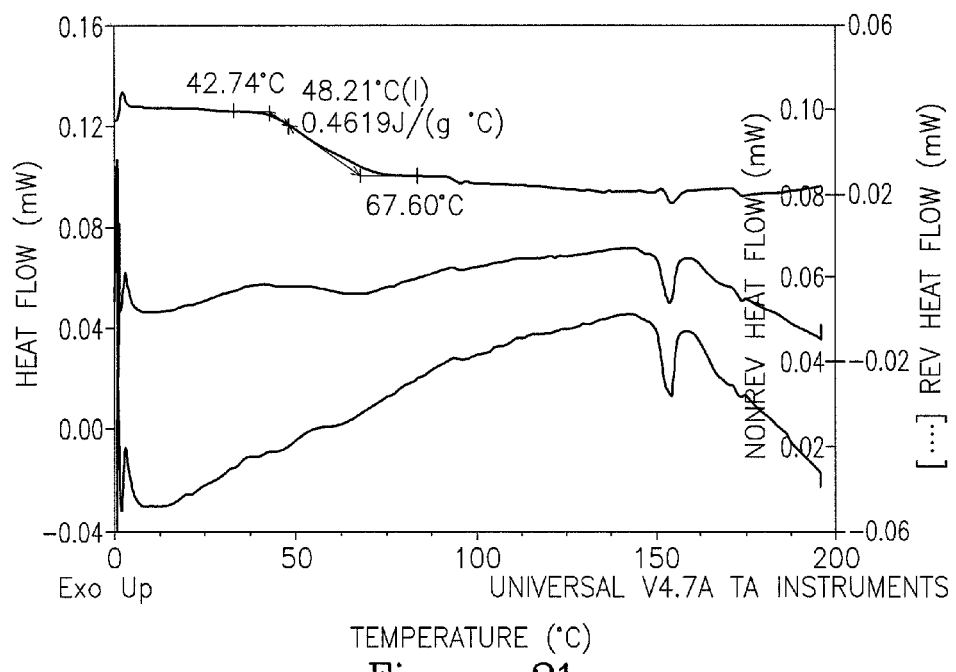
FIG. 21 illustrates a characteristic modulated Differential Scanning calorimetry (mDSC) profile of an amorphous form of apremilast obtained by method IV.
Figure 22:
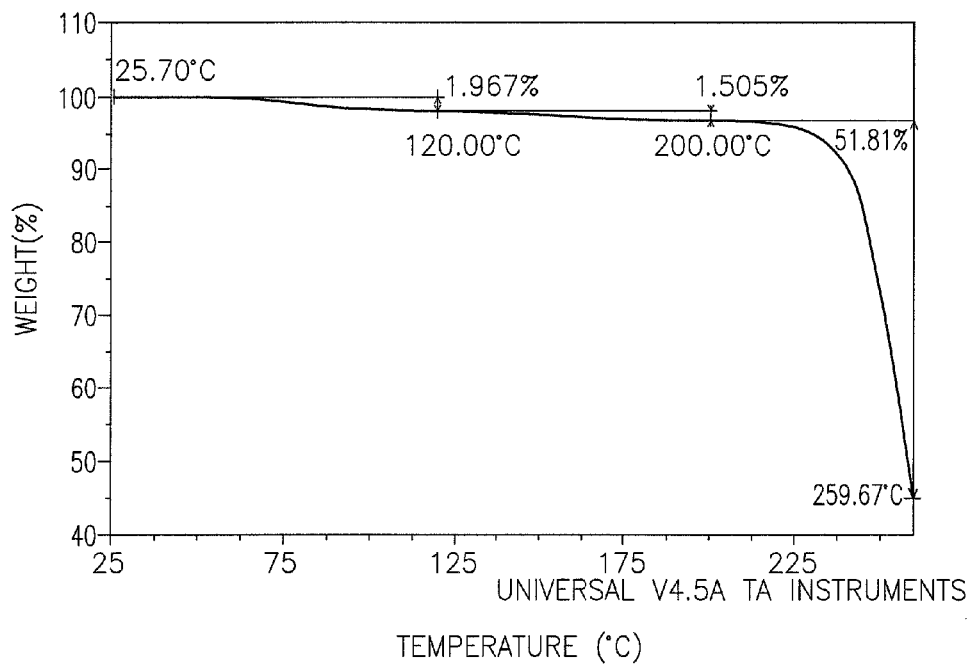
FIG. 22 illustrates a characteristic Thermogravimetric analysis (TGA) profile of an amorphous form of apremilast obtained by method IV.

FIG. 20 (panel A) shows a characteristic XRPD of amorphous apremilast obtained by this method. Also shown for comparison is the X-ray diffraction pattern of the crystalline apremilast Form I (panel B). FIG. 21 illustrates a characteristic modulated DSC profile. The glass transition temperature is 48.2° C. FIG. 22 shows a characteristic TGA profile with a weight loss of about 1.98% between about 26° C. and about 120° C., and a weight loss of about 1.51% between about 120° C. and about 200° C.

Example 6: Scale Up of Amorphous Apremilast (Method III)

Figure 23:
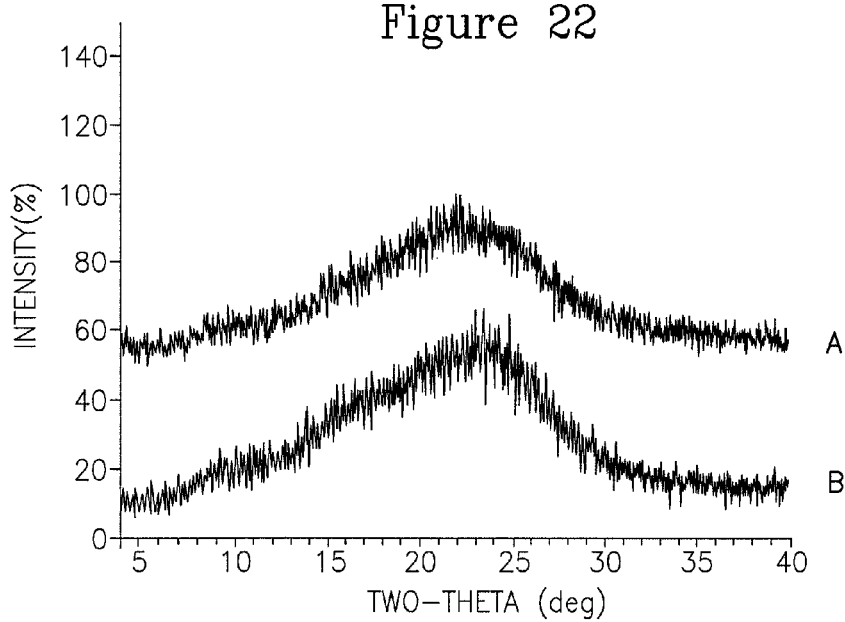
FIG. 23 illustrates a characteristic X-ray diffraction pattern of an amorphous form of apremilast obtained by scaled-up method III (addition of water to acetone; panel A). Also shown for comparison is the X-ray diffraction pattern of the amorphous form of apremilast obtained on a small scale by the same method (panel B).
Figure 24:
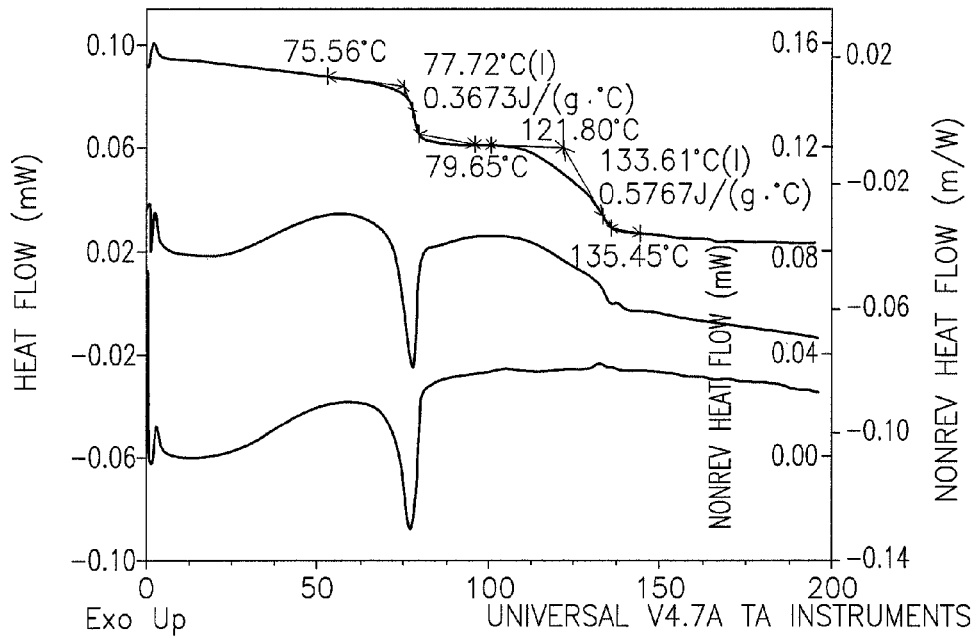
FIG. 24 illustrates a characteristic modulated Differential Scanning calorimetry (mDSC) profile of an amorphous form of apremilast obtained by scaled-up method III (addition of water to acetone).

General method III was scaled-up. Thus, about 5 gr of apremilast (Form I) was dissolved in 50 mL acetone at room temperature to afford a clear solution and then filtered into a glass vial. Then about 10 fold volume of water (the anti-solvent) was quickly added and stirred into the clear apremilast solution until precipitation formed. Once the precipitant formed, it was filtered and dried in vacuum drier at 25° C. The procedure afforded the amorphous apremilast in 81.8% yield. FIG. 23 shows a characteristic XRPD profile of the amorphous form of apremilast obtained by this method (panel A). Also shown in FIG. 23 panel (B) for comparison, is the X-ray diffraction pattern profile of the amorphous form of apremilast obtained on a small scale by the same method as described in Example 4. FIG. 24 illustrates a characteristic modulated DSC profile of amorphous apremilast prepared by this method. The glass transition temperature of the amorphous form obtained by this method is 77.7° C. and 133.6° C. FIG. 25 illustrates a characteristic TGA profile of the amorphous apremilast prepared by this method, with a weight loss of about 0.44% between about 25° C. and about 100° C. and a weight loss of about 0.16% between about 100° C. and about 200° C. FIG. 26 shows a characteristic DVS isotherm plot of amorphous apremilast prepared by this method with a weight gain of about 1.64% from about 0% and about 80% RH. Based on the DVS data (FIGS. 26A and 26B), Table 1 and according to the Hygroscopicity Definitions described in Example 1, the amorphous apremilast is classified as "slightly hygroscopic".

TABLE 1

DVS Isotherm Data.

| | Target | Change In Mass (%) - ref | | |
|---|---|---|---|---|
| | % P/Po | Sorption | Desorption | Hysteresis |
| Cycle 1 | 0.0 | −0.010 | −0.066 | |
| | 5.0 | 0.183 | 0.138 | −0.045 |
| | 10.0 | 0.314 | 0.308 | −0.006 |
| | 15.0 | 0.434 | 0.463 | 0.030 |
| | 20.0 | 0.540 | 0.606 | 0.066 |
| | 25.0 | 0.633 | 0.740 | 0.107 |
| | 30.0 | 0.730 | 0.860 | 0.131 |
| | 35.0 | 0.821 | 0.976 | 0.155 |
| | 40.0 | 0.909 | 1.090 | 0.181 |
| | 45.0 | 1.003 | 1.203 | 0.200 |
| | 50.0 | 1.087 | 1.311 | 0.224 |
| | 55.0 | 1.173 | 1.411 | 0.238 |
| | 60.0 | 1.263 | 1.514 | 0.250 |
| | 65.0 | 1.360 | 1.619 | 0.258 |
| | 70.0 | 1.460 | 1.730 | 0.270 |
| | 75.0 | 1.498 | 1.836 | 0.338 |
| | 80.0 | 1.634 | 1.940 | 0.306 |
| | 85.0 | 1.763 | 1.972 | 0.208 |
| | 90.0 | 1.834 | 1.956 | 0.122 |
| | 95.0 | 1.883 | 1.883 | |

Example 7: Physical Stability of the Amorphous Apremilast (Method III)

About 40 mg of scaled up amorphous sample prepared by solvent-anti-solvent precipitation (addition of water to acetone) as described in Example 6 was weighed into glass vials. The vials were stored under different testing conditions (25° C. closed vial, 25° C./60% RH, 40° C. closed vial and 40° C./75% RH) 1 week, 2 weeks, 4 weeks, and 3 months. The original scaled up amorphous form was used as a control. XRPD and mDSC were checked at the end of each time point.

FIGS. 27-30 show a characteristic XRPD profile of the scaled up amorphous form of apremilast stored under the different testing conditions for one week, two weeks, four weeks and three months (panels A-E, respectively). Apremilast was stable for three months under all testing conditions (25° C. closed, 25° C./60% RH, and 40° C. closed) except at 40° C./75% RH. The color of the apremilast powder was changed from light yellow to darkened yellow at 40° C./75% RH at the third month, while no change was seen for other conditions and time points (Table 3).

FIGS. 31-34 illustrate a characteristic mDSC profile of the scaled up amorphous form of apremilast obtained and stored under the conditions described herein. As shown in these figures and in Table 4, the first glass transition temperature of the amorphous form (77.7° C.) did not change significantly at all testing conditions including also at the end of the third month. This is compared to the second glass transition temperature (133.6° C.) which changed irregularly and even disappeared at different testing conditions at the first week and second week.

Figure 30:
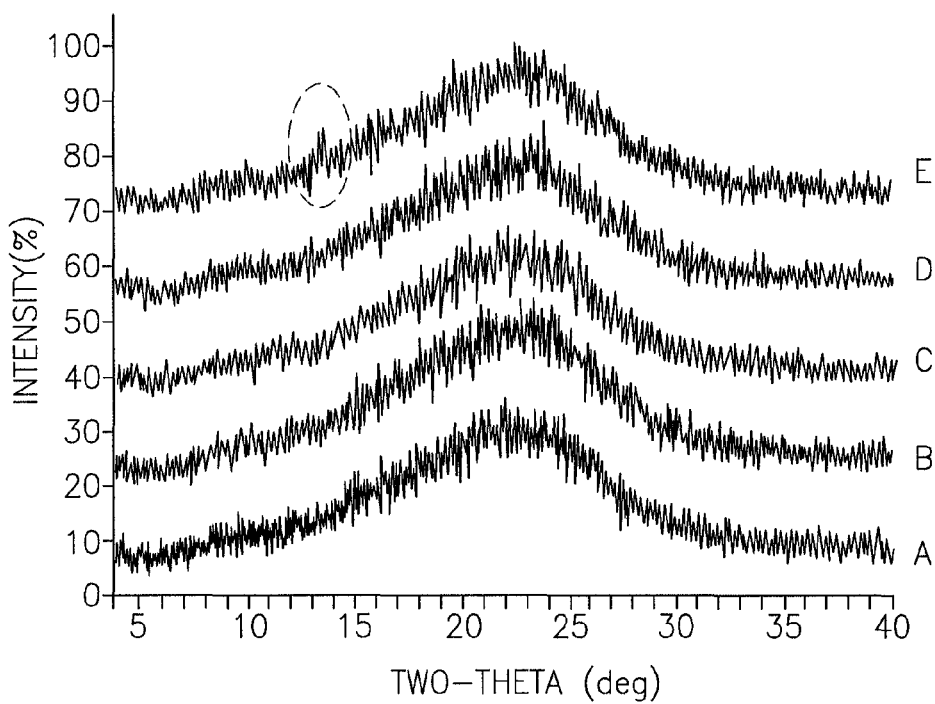
FIG. 30 illustrates a characteristic X-ray diffraction pattern of an up amorphous form of apremilast obtained by scaled-up method III (addition of water to acetone). The apremilast was stored at 40° C./75% RH. Panels A-E represent the following time points: (A) initial time (t=0; control); (B) after one week; (C) after two weeks; (D) after four weeks; and (E) after 3 months.
Figure 31:
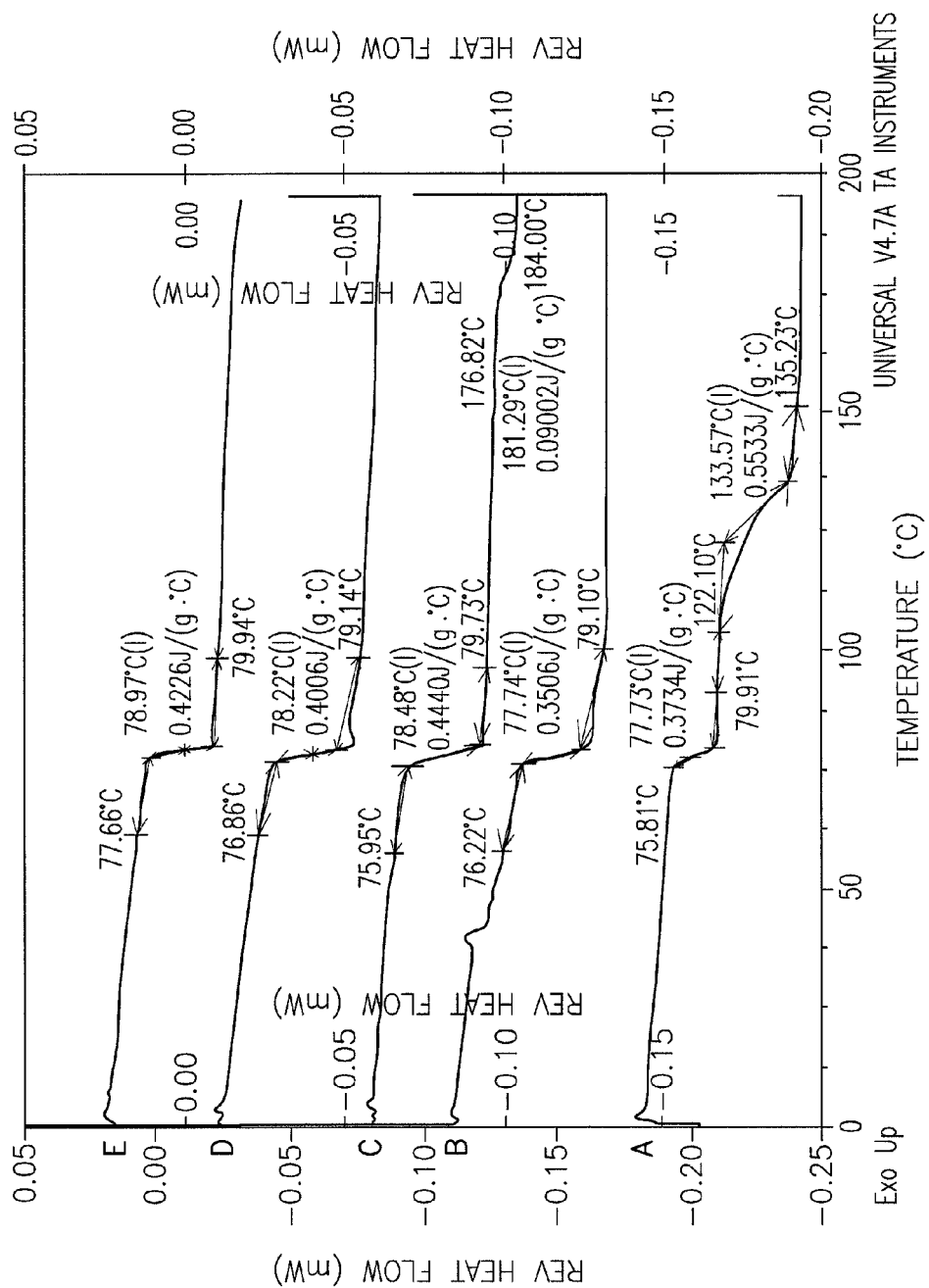
FIG. 31 illustrates a characteristic modulated Differential Scanning calorimetry (mDSC) profile of an amorphous form of apremilast obtained by scaled-up method III (addition of water to acetone). The apremilast was stored at 25° C. in a closed glass vial. Panels A-E represent the following time points: (A) initial time (t=0; control); (B) after one week; (C) after two weeks; (D) after four weeks; and (E) after 3 months.
Figure 32:
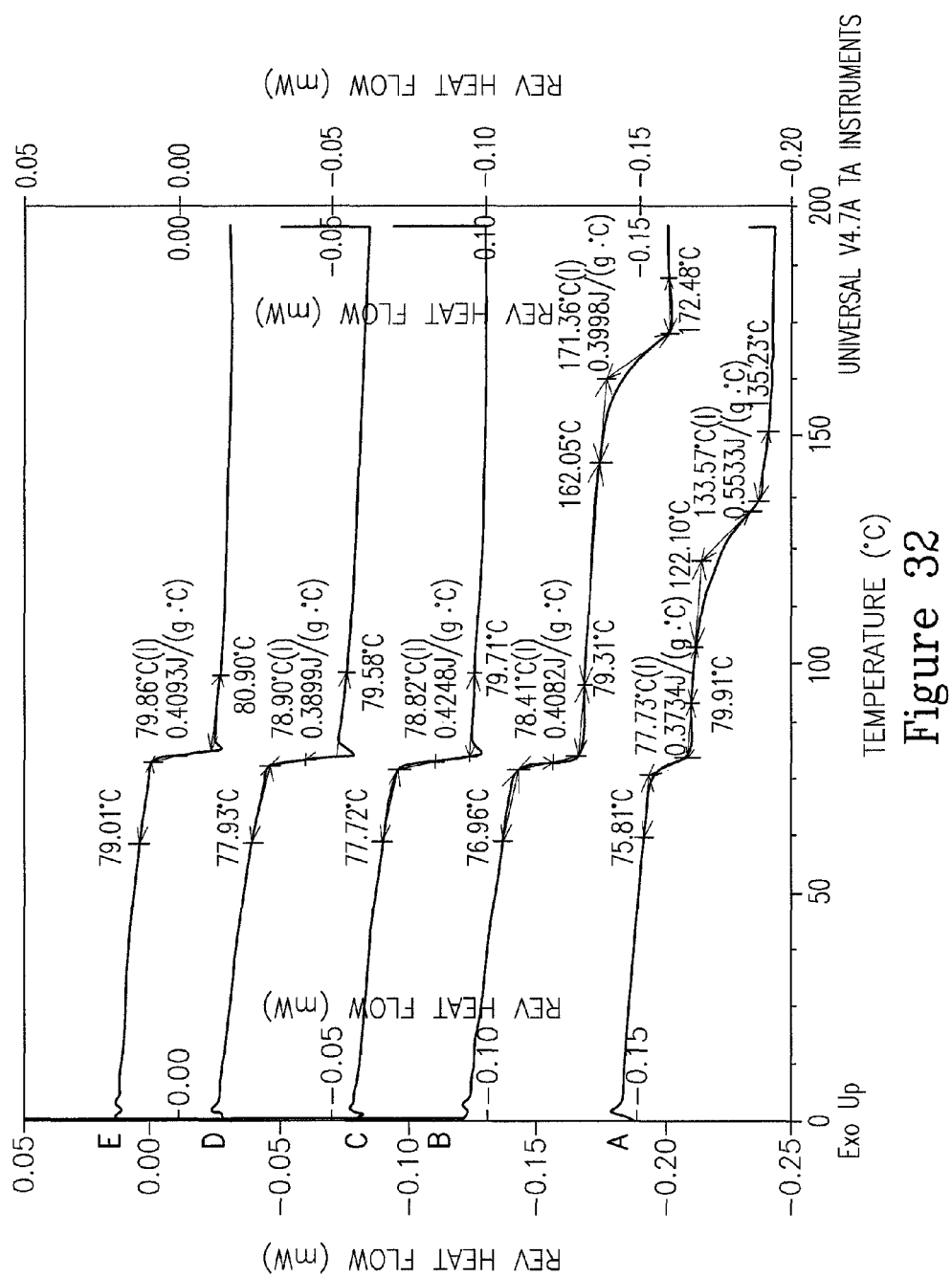
FIG. 32 illustrates a characteristic modulated Differential Scanning calorimetry (mDSC) profile of an amorphous form of apremilast obtained by scaled-up method III (addition of water to acetone). The apremilast was stored at 25° C./60% RH. Panels A-E represent the following time points: (A) initial time (t=0; control); (B) after one week; (C) after two weeks; (D) after four weeks; and (E) after 3 months.
Figure 33:
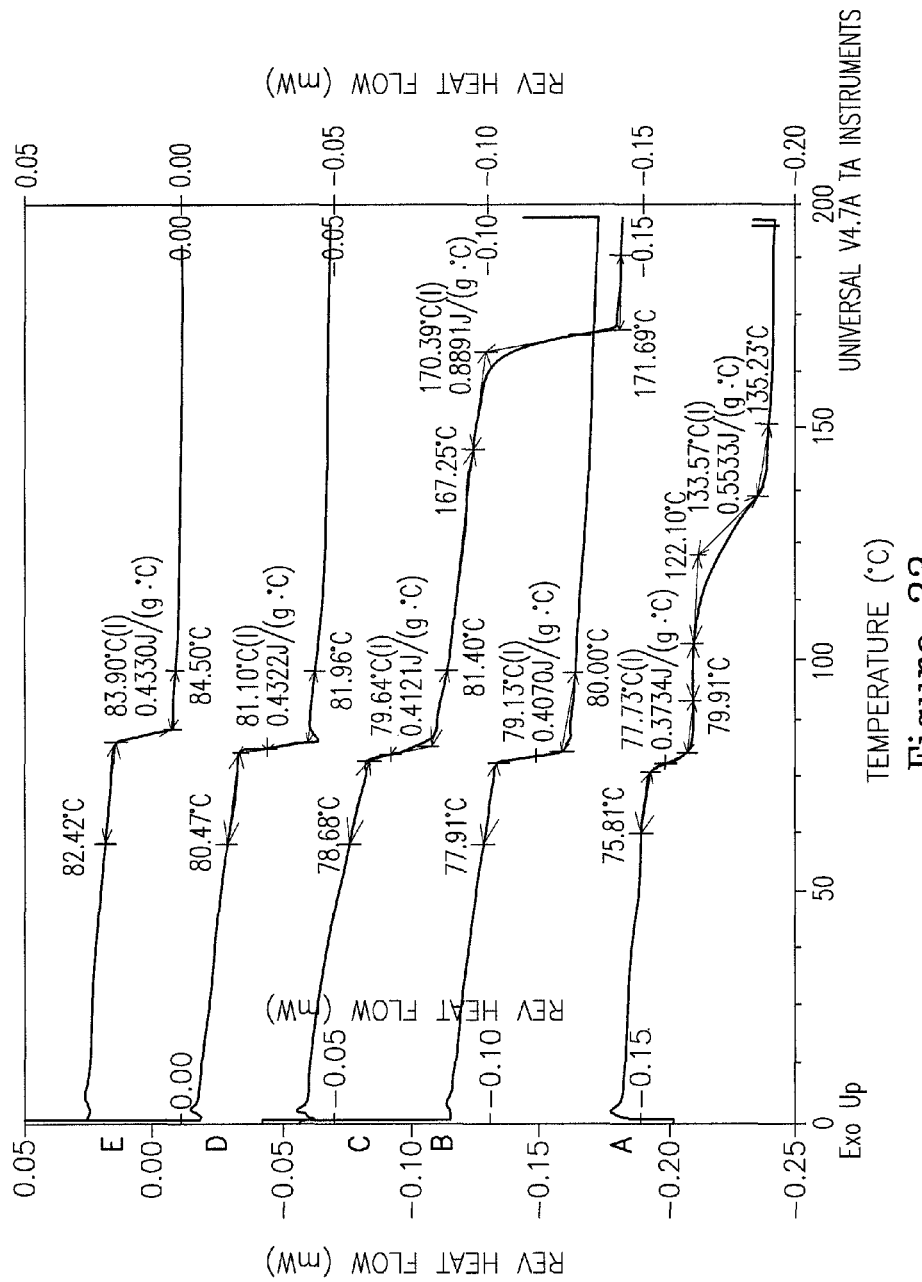
FIG. 33 illustrates a characteristic modulated Differential Scanning calorimetry (mDSC) profile of an amorphous form of apremilast obtained by scaled-up method III (addition of water to acetone). The apremilast was stored at 40° C. in a closed glass vial. Panels A-E represent the following time points (A) initial time (t=0; control); (B) after one week; (C) after two weeks; (D) after four weeks; and (E) after 3 months.
Figure 34:
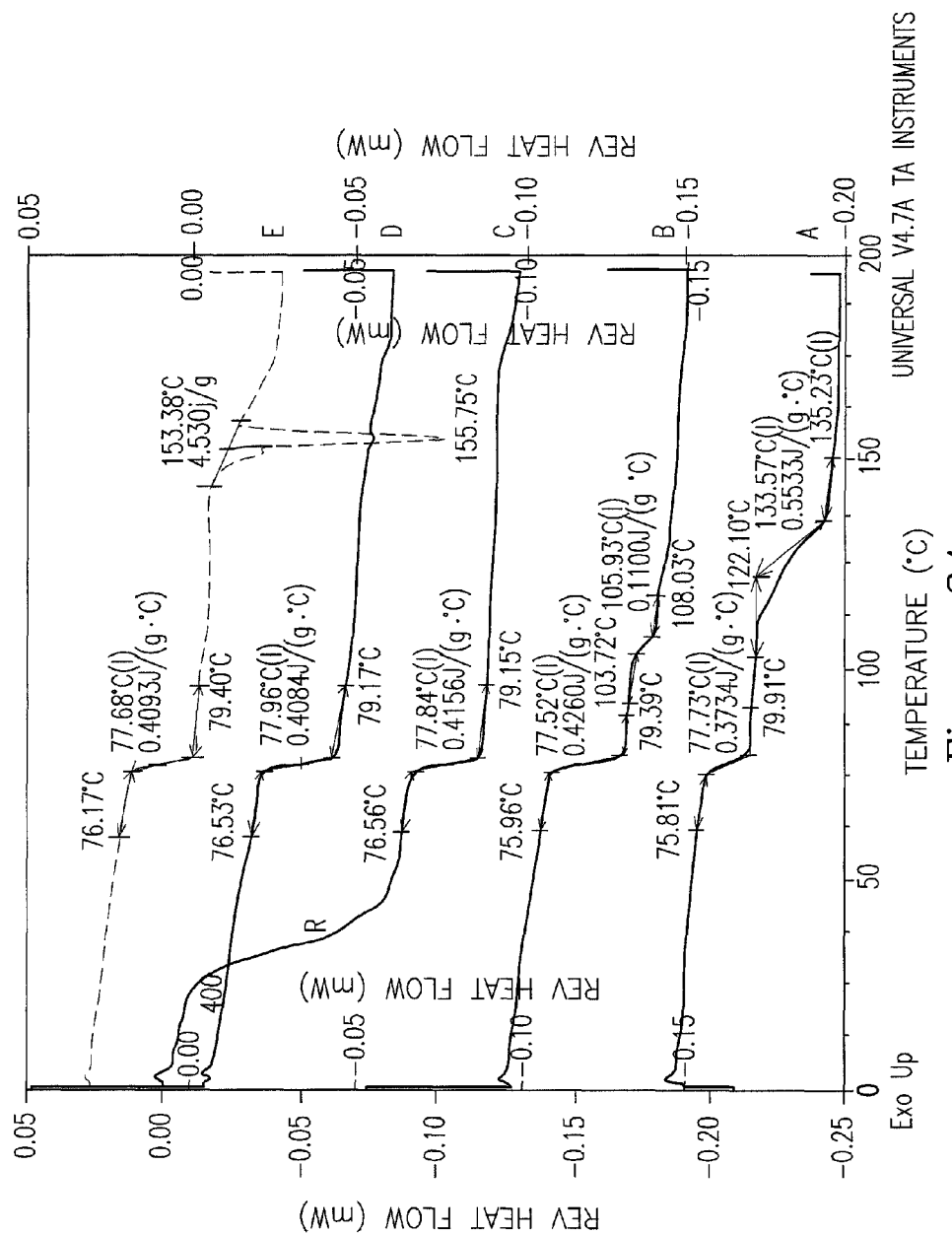
FIG. 34 illustrates a characteristic modulated Differential Scanning calorimetry (mDSC) profile of an amorphous form of apremilast obtained by scaled-up method III (addition of water to acetone). The apremilast was stored at 40° C./75% RH. Panels A-E represent the following time points: (A) initial time (t=0; control); (B) after one week; (C) after two weeks; (D) after four weeks; and (E) after 3 months.

As seen in FIGS. 34-35, a sharp endothermic peak at 153.4° C. was observed at 40° C./75% RH in the third month. This may be related to the melting point of the crystalline form. Further support to this result is in a small spike at 13.5 degrees two theta [2θ°] observed in the XRPD of 40° C./75% RH measured after three months (FIG. 30, panel E, circled). For other time points of 40° C./75% RH such spike was not detected on XRPD. No heat of fusion peak related to crystalline conversion of the samples stored at 25° C. (closed), 40° C. (closed) and 25° C./60% RH for three months was observed.

The amorphous samples at 40° C./75% RH of the second week, fourth week, third month and apremilast Form I were further characterized by DSC at a heating rate of 50° C./min (FIG. 36). The higher heating rate was used to better quantify the crystalline content in the sample by minimizing the crystallization during the heating process. Comparison of the heat fusion showed that there was a small amount (about 5%, estimated by heat of fusion) of crystal formed in the amorphous sample at 40° C./75% RH at the third month.

TABLE 2

XRPD Pattern of Amorphous Apremilast

| | XRPD Pattern | | | |
|---|---|---|---|---|
| Condition | 1st week | 2nd week | 4th week | 3rd month |
| Initial | Amorphous | | | |
| 25° C. Closed | Amorphous | Amorphous | Amorphous | Amorphous |
| 25° C./60% RH | Amorphous | Amorphous | Amorphous | Amorphous |
| 40° C. Closed | Amorphous | Amorphous | Amorphous | Amorphous |
| 40° C./75% RH | Amorphous | Amorphous | Amorphous | Amorphous |

TABLE 3

Appearance of Amorphous Apremilast

| | Appearance | | | |
|---|---|---|---|---|
| Condition | 1st week | 2nd week | 4th week | 3rd month |
| Initial | Light Yellow | | | |
| 25° C. Closed | Light Yellow | Light Yellow | Light Yellow | Light Yellow |
| 25° C./60% RH | Light Yellow | Light Yellow | Light Yellow | Light Yellow |
| 40° C. Closed | Light Yellow | Light Yellow | Light Yellow | Light Yellow |
| 40° C./75% RH | Light Yellow | Light Yellow | Light Yellow | Darken Yellow |

TABLE 4

Tg of mDSC of Amorphous Apremilast

| | Tg of mDSC (° C.) | | | |
|---|---|---|---|---|
| Condition | 1st week | 2nd week | 4th week | 3rd month |
| Initial | 77.7, 133.5 | | | |
| 25° C. Closed | 77.7 | 78.5, 181.3 | 78.2 | 79.0 |
| 25° C./60% RH | 78.4, 171.4 | 78.8 | 78.9 | 79.9 |
| 40° C. Closed | 79.1 | 79.7, 170.4 | 81.1 | 83.9 |
| 40° C./75% RH | 77.5, 105.9 | 77.8, 174.5 | 78.0 | 77.7 |

In conclusion, eleven conditions to prepare amorphous form were found by slow precipitation from solutions (Method I), solid thermal heating/cooling (Method II), solvent-anti-solvent precipitation (Method III) and drying of solvates/hydrates (Method IV). The amorphous form obtained by slow solid thermal heating/cooling method and by adding water to acetone precipitation method showed relatively higher glass transition temperature (77.2° C. and 78.2° C., respectively) which suggested more stable and less residual solvent or water (0.29% and 0.84%) than those obtained by other methods.

The amorphous apremilast obtained by addition of water to acetone precipitation method was scaled up with 81.8% yield. The residual acetone and/or water showed about 0.44% based on TGA-MS measurement. The amorphous apremilast could be classified as slightly hygroscopic (1.64% weight gain from 0% to 80% RH) based on DVS isotherm analysis. It has good physical stability under different testing conditions (25° C. closed, 25° C./60% RH, 40° C. closed) at the end of three months. For 40° C./75% RH condition, a sharp endothermic peak at 153.4° C. related to the melting point of the crystalline form was observed on mDSC for the third month, and a small spike at 13.5 degrees two theta [2θ°] on the XRPD conform well with the mDSC result. About 5% of crystal form in amorphous sample at 40° C./75% RH for three month was estimated by DSC at the higher heating rate (50° C./min) which could be better quantify the crystalline content in the sample by minimizing the crystallization during the heating process. No heat of fusion peak related to crystalline conversion of the samples stored at 25° C. (closed), 40° C. (closed) and 25° C./60% RH for three months was observed. This indicated the amorphous sample may have a higher risk of crystallization under high temperature and high humidity condition.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. An amorphous form of apremilast characterized by an X-ray diffraction (XRD) profile substantially as shown in any of the FIG. 1, 4, 7, 10, 13, 20, 23, 27, 28, 29 or 30.

2. The amorphous apremilast according to claim 1, characterized by a modulated DSC (mDSC) profile substantially as shown in any of the FIG. 2, 5, 8, 11A, 11B, 14, 16, 18, 21, 24, 31, 32, 33, 34 or 35, or a DSC profile substantially as shown in FIG. 36.

3. The amorphous apremilast according to claim 2, having a glass transition temperature between about 36° C. and about 79° C.

4. The amorphous apremilast according to claim 3, having a glass transition temperature at about 36.1° C., 38.0° C., 41.9° C., 44.1° C., 48.2° C., 60.9° C., 75.9° C. 77.2° C., 77.7° C., 78.2° C., or about 133.6° C.

5. The amorphous apremilast according to claim 1, characterized by a TGA profile substantially as shown in any of the FIG. 3, 6, 9, 12, 15, 17, 19, 22 or 25.

6. The amorphous apremilast according to claim 1, characterized by a Dynamic Vapor Sorption profile substantially as shown in FIGS. 26A and 26B.

7. A pharmaceutical composition comprising as an active ingredient the amorphous form of apremilast according to claim 1 and a pharmaceutically acceptable carrier.

8. A method of treating a medical condition mediated by phosphodiesterase 4 (PDE4) or TNFα, the medical condition selected from the group consisting of psoriasis, psoriatic arthritis, ankylosing spondylitis, Behcet's disease, and rheumatoid arthritis, comprising administering to a subject in need thereof an effective amount of the amorphous form of apremilast according to claim 1, or a pharmaceutical composition comprising said amorphous apremilast.

9. An amorphous form of apremilast according to claim 1, prepared by the process comprising the steps of:
  (a) heating apremilast to melt under vacuum; and
  (b) cooling the melted apremilast obtained in step (a), so as to provide amorphous apremilast.

10. The amorphous apremilast according to claim 9, wherein the cooling in step (b) is selected from fast cooling and slow cooling.

11. An amorphous form of apremilast according to claim 1, prepared by the process comprising the steps of:
  (a) dissolving apremilast in a solvent or a mixture of solvents selected from THF, acetone and DMF:EtOH; and
  (b) slowly evaporating the solvent or a mixture of solvents so as to precipitate an amorphous apremilast.

12. An amorphous form of apremilast according to claim 1, prepared by the process comprising the steps of:
  (a) dissolving apremilast in a solvent selected from acetone, THF and MEK to obtain an apremilast solution; and
  (b) combining the apremilast solution with an anti-solvent selected from water and heptane so as to precipitate amorphous apremilast.

13. The amorphous apremilast according to claim 12, wherein the process
  comprises adding the apremilast solution to the anti-solvent; or adding the anti-solvent to the apremilast solution.

14. The amorphous form of apremilast according to claim 12, wherein i. the solvent/anti-solvent mixture is heptane and acetone, wherein heptane is added to acetone; or
ii. the solvent/anti-solvent mixture is heptane and acetone, wherein acetone is added to heptane; or
iii. the solvent/anti-solvent mixture is heptane and MEK, preferably wherein heptane is added to MEK; or
iv. the solvent/anti-solvent mixture is THF and heptane, preferably wherein THF is added to heptane; or
v. the solvent/anti-solvent mixture is water and acetone, preferably wherein water is added to acetone.

15. The amorphous apremilast according to claim 12, wherein the process further comprises the step of drying the amorphous apremilast obtained in step (b) under vacuum at a temperature of about 25° C.

16. An amorphous form of apremilast according to claim 1, prepared by the process comprising the steps of:
(a) heating apremilast to a temperature of about 120° C.; and
(b) cooling the apremilast obtained in step (a) to about 25° C., so as to provide amorphous apremilast.

17. A process for preparing an amorphous apremilast according to claim 1, comprising the steps of:
(a) heating apremilast to melt under vacuum; and
(b) cooling the melted apremilast obtained in step (a), so as to provide amorphous apremilast.

18. A process for preparing an amorphous apremilast according to claim 1, comprising the steps of:
(a) dissolving apremilast in a solvent or a mixture of solvents selected from THF, acetone and DMF:EtOH; and
(b) slowly evaporating the solvent or a mixture of solvents so as to precipitate an amorphous apremilast.

19. A process for preparing an amorphous apremilast according to claim 1, comprising the steps of:
(a) dissolving apremilast in a solvent selected from acetone, THF and MEK to obtain an apremilast solution; and
(b) combining the apremilast solution with an anti-solvent selected from water and heptane so as to precipitate amorphous apremilast.

20. A process for preparing an amorphous apremilast according to claim 1, comprising the steps of:
(a) heating apremilast to a temperature of about 120° C.; and
(b) cooling the apremilast obtained in step (a) to about 25° C., so as to provide amorphous apremilast.

* * * * *